United States Patent
Koch et al.

(10) Patent No.: US 11,878,153 B2
(45) Date of Patent: *Jan. 23, 2024

(54) PORTABLE INFUSION PUMP

(71) Applicant: SHL MEDICAL AG, Zug (CH)

(72) Inventors: Eugen Koch, Essel (DE); Cheng-Jung Yang, Kaohsiung (TW); Laura Scholze, Munich (DE)

(73) Assignee: SHL MEDICAL AG, Zug (CH)

( * ) Notice: Subject to any disclaimer, the term of this patent is extended or adjusted under 35 U.S.C. 154(b) by 635 days.

This patent is subject to a terminal disclaimer.

(21) Appl. No.: 17/088,849

(22) Filed: Nov. 4, 2020

(65) Prior Publication Data

US 2021/0046252 A1 Feb. 18, 2021

Related U.S. Application Data

(63) Continuation of application No. 15/989,509, filed on May 25, 2018, now Pat. No. 10,881,811, which is a
(Continued)

(30) Foreign Application Priority Data

Oct. 23, 2013 (SE) .................................... 1351259-5

(51) Int. Cl.
*A61M 5/32* (2006.01)
*A61M 5/145* (2006.01)
(Continued)

(52) U.S. Cl.
CPC ........ *A61M 5/3204* (2013.01); *A61M 5/1424* (2013.01); *A61M 5/1454* (2013.01);
(Continued)

(58) Field of Classification Search
CPC ......... A61M 2005/14256; A61M 2005/31518; A61M 2005/3247; A61M 5/1424;
(Continued)

(56) References Cited

U.S. PATENT DOCUMENTS 4,300,554 A 11/1981 Hessberg et al.
10,010,681 B2 * 7/2018 Koch .................... A61M 5/168
(Continued)

FOREIGN PATENT DOCUMENTS

EP 1326659 B1 12/2005
EP 1276529 B1 6/2006
(Continued)

OTHER PUBLICATIONS

EPO, Int'l Search Report in PCT/EP2014/072655, dated Feb 18, 2015.

*Primary Examiner* — Quynh-Nhu H. Vu
(74) *Attorney, Agent, or Firm* — MCDONNELL BOEHNEN HULBERT & BERGHOFF LLP

(57) ABSTRACT

The present invention relates to a medicament delivery device comprising a housing, a compartment inside said housing for positioning a medicament container, an injection needle arranged to said housing, being connectable to said medicament container for delivering a dose of medicament, a manually operated activation mechanism for activating said device, an actuation mechanism operably connected to said activation mechanism and arranged to, upon activation of said activation mechanism, extend said injection needle from a first position inside said housing to a second position wherein a penetration of a patient is performed, a plunger rod arranged in said housing capable of acting on said medicament container for delivering a dose of medicament through said injection needle, a driver capable of acting on said plunger rod for delivering a dose of medicament. The invention is characterised in that said device comprises a needle cover operably arranged in said housing from a first position inside said housing to a second extended position outside said housing for shielding said injection needle when said injection needle is in said second position.

9 Claims, 25 Drawing Sheets

Related U.S. Application Data continuation of application No. 15/031,582, filed as application No. PCT/EP2014/072655 on Oct. 22, 2014, now Pat. No. 10,010,681.

(51) Int. Cl.
  *A61M 5/142* (2006.01)
  *A61M 5/168* (2006.01)
  *A61M 5/315* (2006.01)

(52) U.S. Cl.
  CPC ........ *A61M 5/14248* (2013.01); *A61M 5/168* (2013.01); *A61M 5/14566* (2013.01); *A61M 2005/14256* (2013.01); *A61M 2005/31518* (2013.01); *A61M 2005/3247* (2013.01)

(58) Field of Classification Search
  CPC ............ A61M 5/14248; A61M 5/1454; A61M 5/14566; A61M 5/168; A61M 5/3204
  See application file for complete search history.

(56) References Cited

U.S. PATENT DOCUMENTS

| | | | |
|---|---|---|---|
| 10,881,811 B2 * | 1/2021 | Koch | A61M 5/1424 |
| 2002/0055711 A1 | 5/2002 | Lavi et al. | |
| 2003/0078546 A1 | 4/2003 | Jensen | |
| 2007/0073236 A1 | 3/2007 | Mernoe et al. | |
| 2009/0093792 A1 * | 4/2009 | Gross | A61M 5/31596 604/218 |
| 2012/0220954 A1 | 8/2012 | Cowe | |
| 2013/0060233 A1 | 3/2013 | O'Connor et al. | |
| 2013/0110049 A1 * | 5/2013 | Cronenberg | A61M 5/3287 604/239 |
| 2013/0253472 A1 | 9/2013 | Cabiri | |
| 2013/0274655 A1 | 10/2013 | Jennings et al. | |
| 2015/0080800 A1 | 3/2015 | Cronenberg | |
| 2015/0126926 A1 | 5/2015 | Giambattista et al. | |
| 2015/0250949 A1 | 9/2015 | Maritan | |
| 2015/0290392 A1 | 10/2015 | Henderson et al. | |
| 2018/0228966 A1 | 8/2018 | Barmaimon et al. | |
| 2018/0304006 A1 * | 10/2018 | Bente, IV | A61M 5/16804 |

FOREIGN PATENT DOCUMENTS

| | | |
|---|---|---|
| EP | 1583573 B1 | 2/2011 |
| EP | 2698180 A1 | 2/2014 |
| JP | 2007-105490 A | 4/2007 |
| JP | 2010-510027 A | 4/2010 |
| JP | 2011-530361 A | 12/2011 |
| JP | 2012-500099 A | 1/2012 |
| WO | 2001/078812 A1 | 10/2001 |
| WO | 02/02165 A2 | 1/2002 |
| WO | 02/28455 A1 | 4/2002 |
| WO | 2004/089448 A1 | 10/2004 |
| WO | 2004/098683 A1 | 11/2004 |
| WO | 2005/025636 A2 | 3/2005 |
| WO | 2010/078227 A1 | 7/2010 |
| WO | 2010/112377 A1 | 10/2010 |
| WO | 2011/090955 A1 | 7/2011 |
| WO | 2012/049468 A2 | 4/2012 |
| WO | 20013/140395 A1 | 9/2013 |
| WO | 2013/148435 A1 | 10/2013 |
| WO | 2013/153041 A2 | 10/2013 |

* cited by examiner

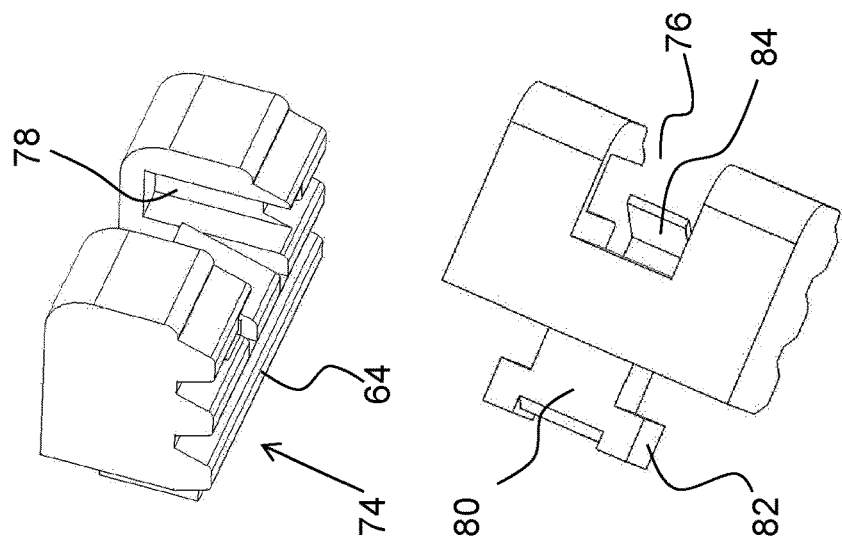
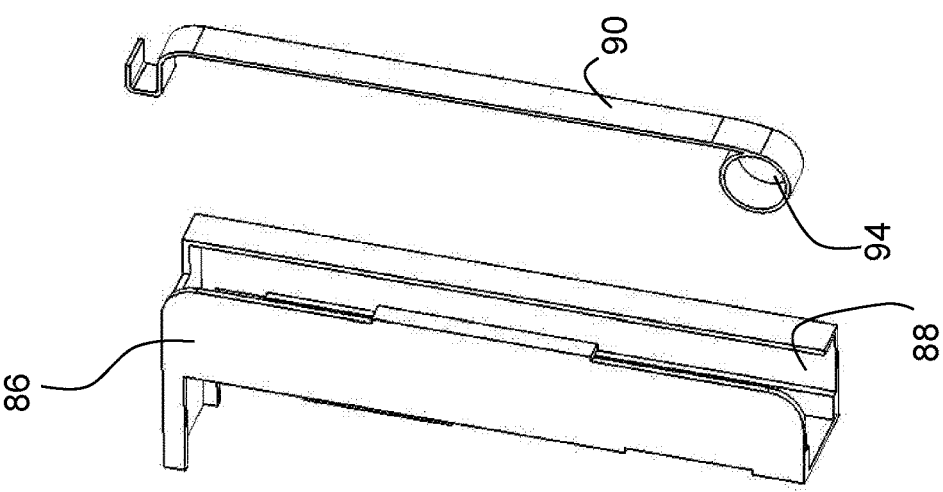
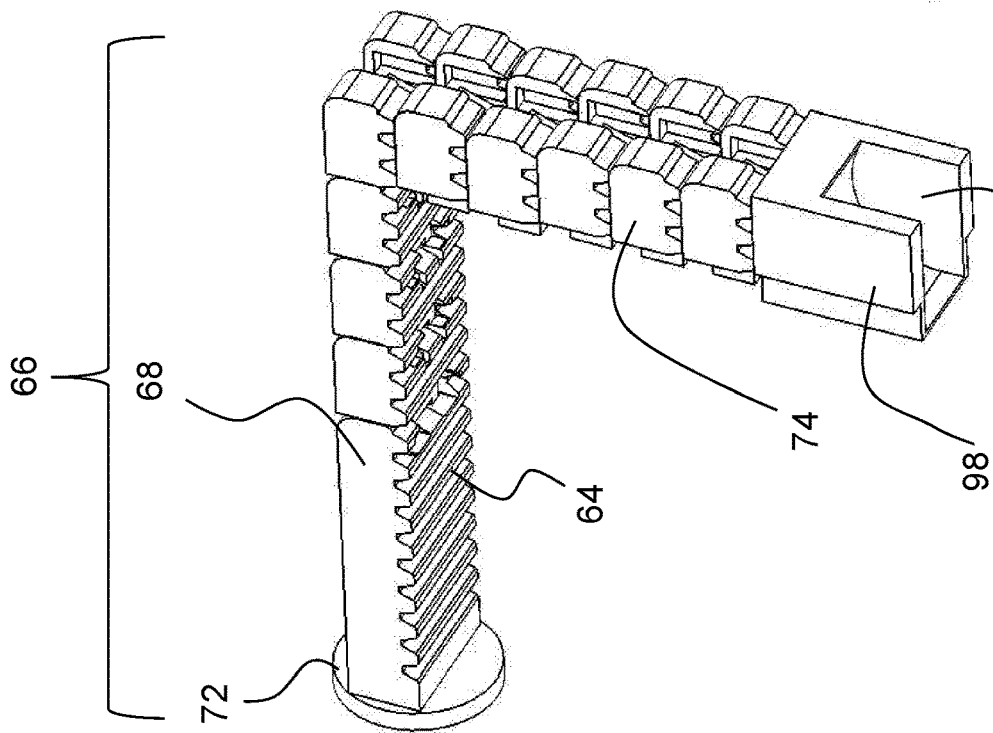

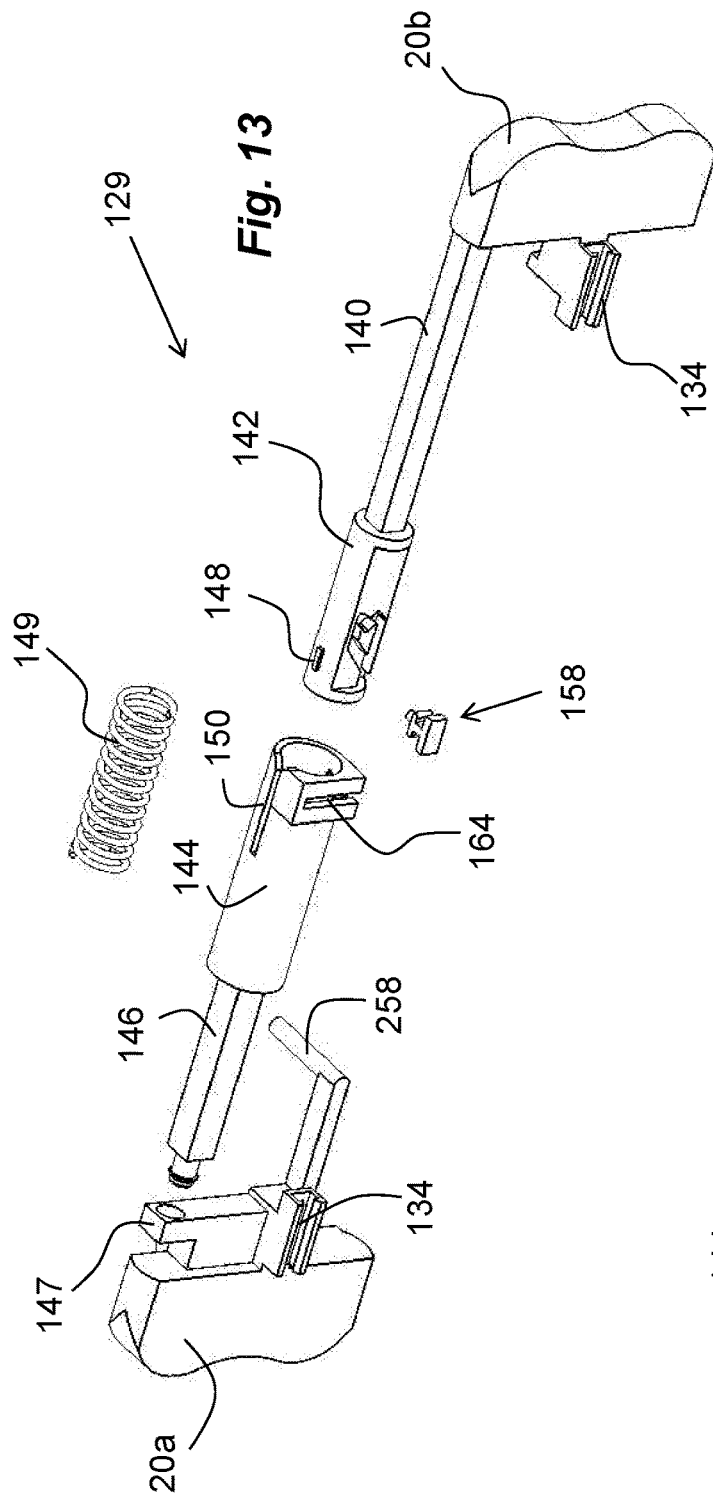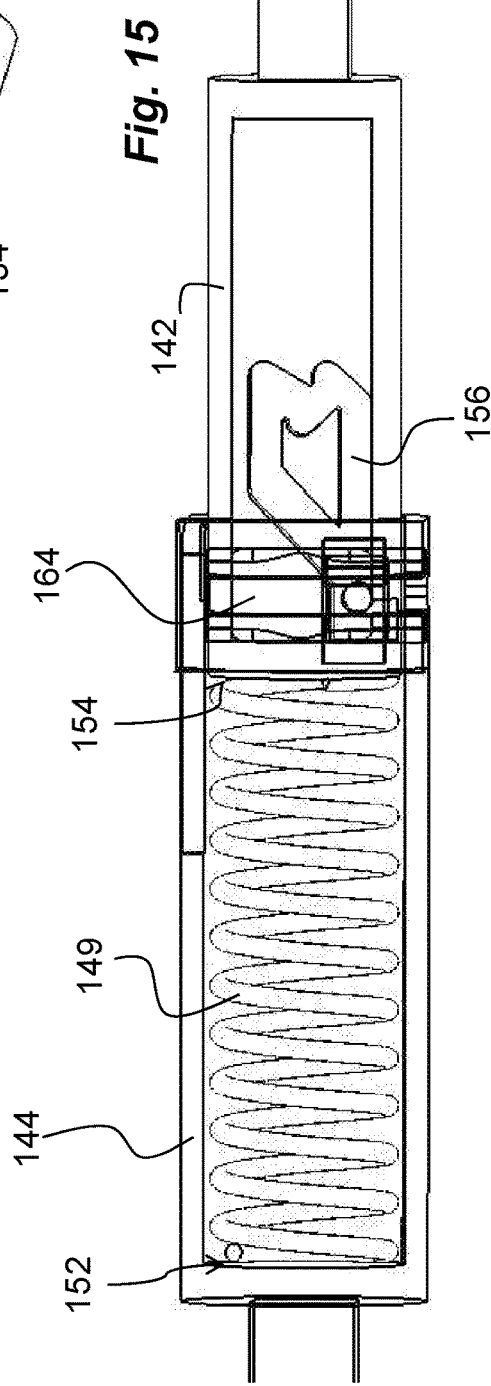

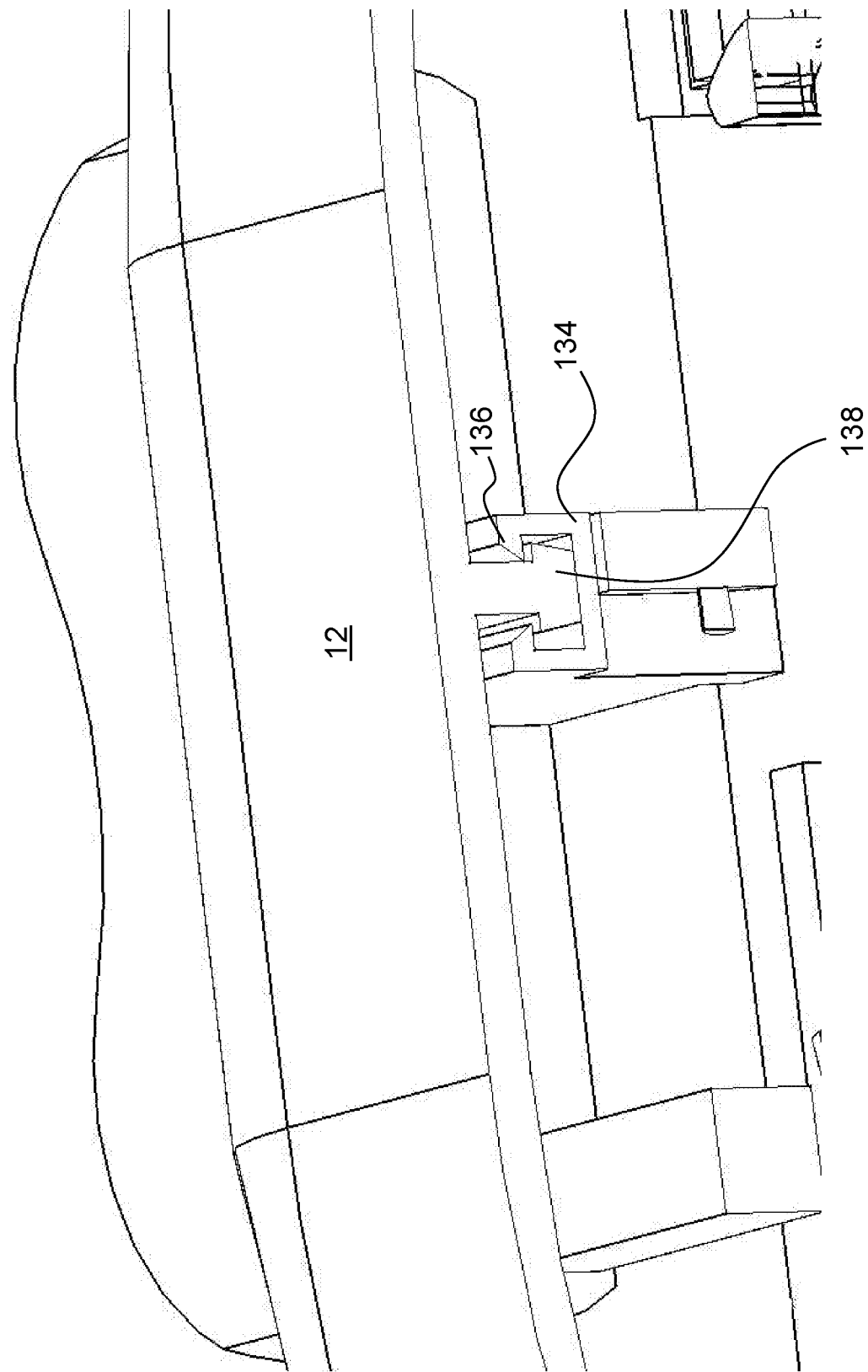

PORTABLE INFUSION PUMP

CROSS REFERENCE TO RELATED APPLICATIONS

The present application is a continuation of U.S. patent application Ser. No. 15/989,509, filed May 25, 2018, which is a continuation of U.S. patent application Ser. No. 15/031,582, filed Apr. 22, 2016, now U.S. Pat. No. 10,010,681, which is a U.S. National Phase Application pursuant to 35 U.S.C. § 371 of International Application No. PCT/EP2014/072655 filed Oct. 22, 2014, which claims priority to Swedish Patent Application No. 1351259-5 filed Oct. 23, 2013. The entire disclosure contents of these applications are herewith incorporated by reference into the present application.

TECHNICAL AREA

The present invention relates to a medicament delivery device and in particular a compact and easy to use infuser.

BACKGROUND

For a number of years infusers have been used that provides the patient or user with the means of administering a drug in an easy way without the need for a medically trained person, such as a physician or nurse to handle the device.

One drawback with these infusers is that they have a medicament container of a certain length as well as a plunger rod acting on said medicament container for delivering a dose of medicament, also having a certain length, whereby the total length of a device has to be at least the length of the medicament container and the plunger rod. If a drive member is used, such as for instance a drive spring, the length of the device is further increased.

One way of handling this is to make at least the plunger rod shorter for not adding so much to the overall length. One solution to this is to have a flexible plunger rod, which is disclosed for example in EP 1 583 573 where the plunger rod may be bent or formed as a circle. Another solution is disclosed in EP 1 276 529 having a bendable plunger rod with a ratchet on a side surface, where the plunger rod is bent around a cogwheel, for driving the plunger rod.

The drawback with these solutions is that the length might not be increased by the whole length of the plunger rod, but at least by some amount because the circle formed by the bent plunger rod also adds to the length. Further, the dimensions of the device in other directions are increased considerably by these solutions, providing a rather bulky device.

The above-mentioned solutions utilize some sort of power spring wound around a shaft or the like positioned in the centre of the circle formed by the curved plunger rod. These power springs often act directly or almost directly on the curved plunger rod, such as with the device of EP 1 276 529 where the power spring acts on the cogwheel.

The drawback with this drive solution is that it complicates the addition of functions such as activation mechanisms, constant injection speed mechanism, automatic stop mechanisms, just to mention a few. This is mainly because the plunger rod surrounds and thereby blocks access to the plunger drive spring without enlarging the device.

Regarding the injection speed control aspect, some solutions have been devised, such as for example in EP 1 326 659 where an electric motor is utilized for driving the flexible plunger rod. Also document WO 2010/112377 discloses a device utilizing electric motors for driving and controlling the movement and speed of the plunger rod.

The drawback with this is that the device has to rely on electric power in order to deliver a dose of medicament. If any batteries used are depleted, the device cannot be used at all, which may be critical for some types of drugs.

Another drawback with many of the mentioned devices is that there is no feature or mechanism for handling the injection needle after completed injection. When the device is withdrawn, the injection needle completely exposed and may cause injuries to persons handling or coming in contact with the device after use.

SUMMARY

In the present application, when the term "distal part/end" is used, this refers to the part/end of the device, or the parts/ends of the members thereof, which under use of the device is located the furthest away from the medicament delivery site of the patient. Correspondingly, when the term "proximal part/end" is used, this refers to the part/end of the device, or the parts/ends of the members thereof, which under use of the device is located closest to the medicament delivery site of the patient.

The aim of the present invention is to remedy the drawbacks of the state of the art medicament delivery devices. This aim is obtained with a medicament delivery device according to the features of the independent patent claim. Preferable embodiments of the invention form the subject of the dependent patent claims.

The medicament delivery device preferably comprises a housing having a compartment inside said housing for positioning a medicament container. The medicament container may have a number of designs that are suitable for delivering a dose of medicament when the device is activated. According to one favourable aspect, the medicament container may be arranged with a stopper that is movable by appropriate means. The medicament container may further be arranged with some connection interface to an injection needle, through which a dose of medicament may be delivered. The connection interface may for example be a septum or other type of membrane or wall that may be penetrated or pierced by a connection element, which connection element may be a pointed end of a conduit in flow communication with the injection needle.

The device may further advantageously comprise a manually operated activation mechanism for activating said device in order to deliver a dose of medicament. The activation mechanism may be operably connected to a number of functions and features of the device.

One such feature may be an actuation mechanism arranged to, upon activation of said activation mechanism, extend the injection needle from a first position inside said housing to a second position wherein a penetration of a patient is performed. Thus, when the device is placed on the body of a patient and the activation mechanism is operated, a penetration of the skin of the patient will be performed by the actuation mechanism, rendering the device ready for delivering a dose of medicament.

In order to provide a dose of medicament from the medicament container through the conduit to the injection needle, the device is preferably provided with a plunger rod in said housing and arranged to act on the stopper of the medicament container. In order to do so, the plunger rod may be operably connected to a driver capable of acting on said plunger rod for delivering a dose of medicament. In this aspect, the driver may advantageously comprise some energy accumulating feature, which energy may drive the plunger rod. The energy accumulating feature may comprise a number of different designs such as compression springs, torsion springs, clock springs, gas springs and the like, just to mention a few.

Preferably the device may comprises a needle cover operably arranged in said housing from a first position inside said housing to a second extended position outside said housing for shielding said injection needle when said injection needle is in said second position. With this solution, the injection needle may be protected when the device is removed from the body of the patient, thereby minimizing the risk of unintentional needle sticks.

According to one feasible solution, the actuation mechanism may comprise a locking mechanism capable of locking said injection needle in said second position. This ensures that the penetration depth of the injection needle is maintained during the subsequent injection sequence. Thus, it is not required for the user to operate the activation mechanism after the injection needle has reached the second penetration position.

Further, another favourable feature, the needle cover may comprise locking elements operably arranged to lock said needle cover in said second position. This further minimizes the risk of injuries of the injection needle since the needle cover is locked from movement.

According to another favourable feature, the activation mechanism may comprise two operating elements placed on opposite sides of said device. This solution of the activation of the device is advantageous since the operating elements may be operated by one hand of the user gripping the device. According to a further favourable solution, the operating elements may comprise activation buttons, which buttons are manually depressed for activating said device. Since the buttons are placed on opposite sides of the device, the forces for depressing the buttons are directed towards each other. Thus the forces will not affect the position of the device on the body of the patient, which is an advantage during the penetration and the injection sequence, because any movement of the device when the injection needle has penetrated the body will cause pain and discomfort.

According to one feasible solution, the activation buttons may be connected to said injection needle via a linkage comprised in said actuation mechanism, thereby enabling movement of said injection needle to said extended position when said buttons are depressed. The linkage thus enables movement of the injection needle in directions deviating from the movement directions of the activation buttons, for example a direction ninety degrees in relation to the activation buttons. When using a linkage, the locking mechanism of said injection needle may preferably be comprised in the linkage.

In order to ascertain a smooth and more or less constant injection speed, the device may further comprise an injection speed control mechanism operatively connected to said driver. With such a mechanism, the injection speed may be chosen and controlled in a positive manner. This may be an important feature for medicament solutions that for example are painful when delivered in larger quantities quickly. The dose delivery may then be set and controlled to deliver very small quantities continuously for longer time periods.

According to one feasible solution, the injection speed control mechanism may for example comprise a pallet fork acting on an escapement wheel, as well as a transmission between said drive means and said escapement wheel. This solution provides possibilities of a choosing and changing injection speeds in a wide range. The use of a transmission enables the choice of gearing those suites the delivery speed of a certain medicament. In order to provide a certain injection speed, the escapement wheel is preferably drivably connected to a drive spring.

According to another preferable solution, the device may further comprise an auto-stop mechanism capable of permanently stopping said injection speed control mechanism at the end of a dose delivery sequence. Thereby it is clearly indicated to a user that the injection is completed and that the device may be removed from the patient.

To further enhance the usability of the device, it may further comprise a manually operable stop mechanism capable of permanently stopping said injection speed control mechanism upon activation. This may for example be an advantage in a situation when the user for some reason has to remove the device from the body. The stop mechanism will then ascertain that no medicament is expelled from the device after removal.

According to another feasible solution, the device may further comprise a manually operated pausing mechanism capable of temporarily stopping and subsequent starting of the injection speed control mechanism upon activation. This may for example be an advantage when the user has started the injection sequence but wants to pause it for some reason. The injection speed control mechanism is then stopped only temporary and may be resumed by the user. The pausing mechanism may for example by operably connected to the activation mechanism.

According to another feasible solution, the device may also comprise a medicament container penetration mechanism operably connected to said activation mechanism for creating, upon activation, a communication between the medicament inside said medicament container and said injection needle. In this manner, the content of the medicament container is not affected in any way before the device is activated. Thus, the medicament container may be inserted into the device at any time without the risk of degrading the medicament, because a passage between the interior of the medicament container and the injection needle is only obtained after activation of the device.

These and other aspects of, and advantages with, the present invention will become apparent from the following detailed description of the invention and from the accompanying drawings.

BRIEF DESCRIPTION OF THE FIGURES

In the following detailed description of the invention, reference will be made to the accompanying drawings, of which

FIG. 9 illustrates detailed views of components and mechanisms comprised in the device of FIG. 1;

FIGS. 10a and 10b show two different views of the same component of the device of FIG. 1;

FIGS. 11-17 show detailed views of components and mechanisms comprised in the device of FIG. 1;

DETAILED DESCRIPTION

Figure 1:
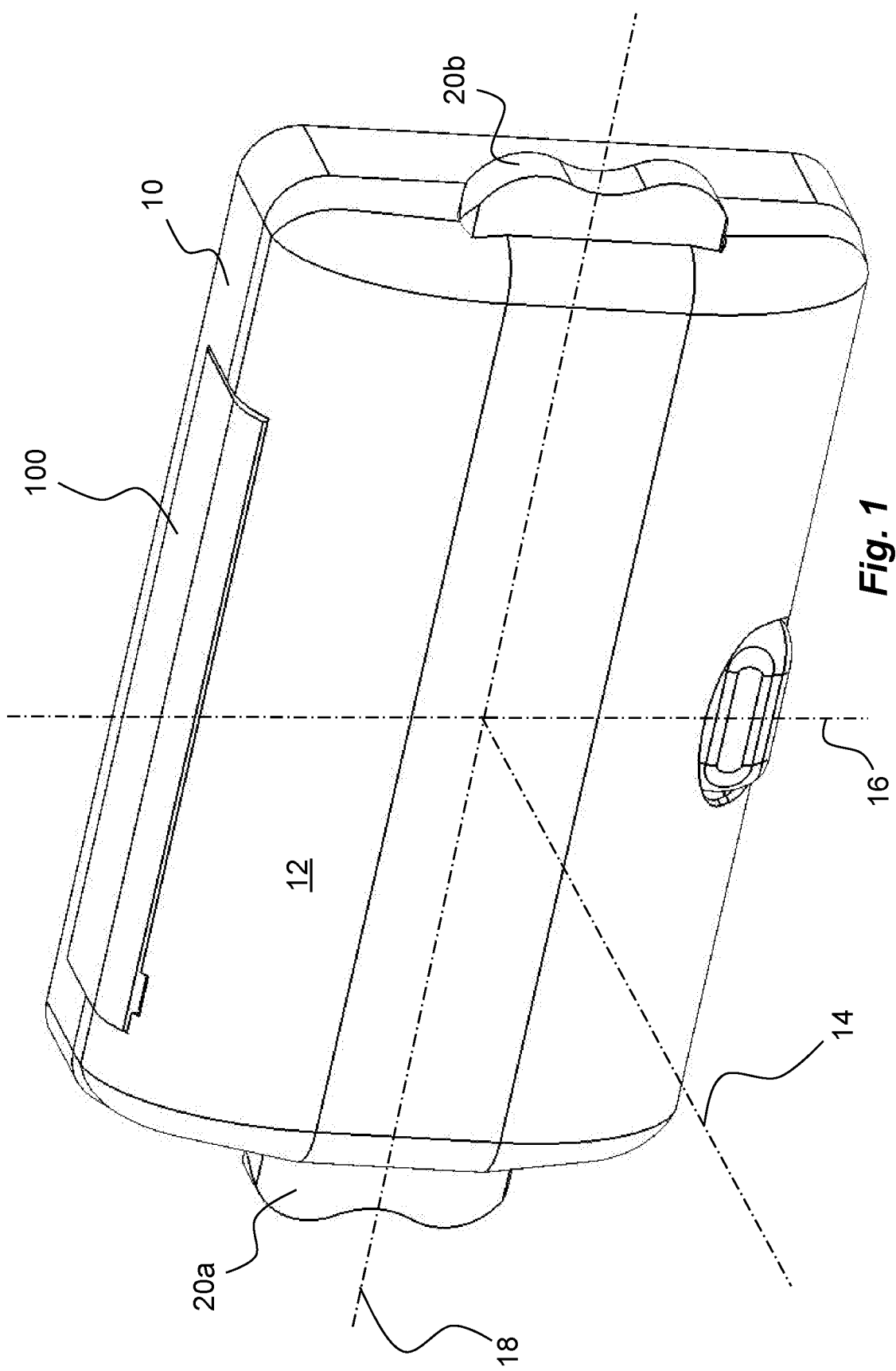
FIG. 1 is a perspective view of an embodiment of a medicament delivery device.
Figure 2:
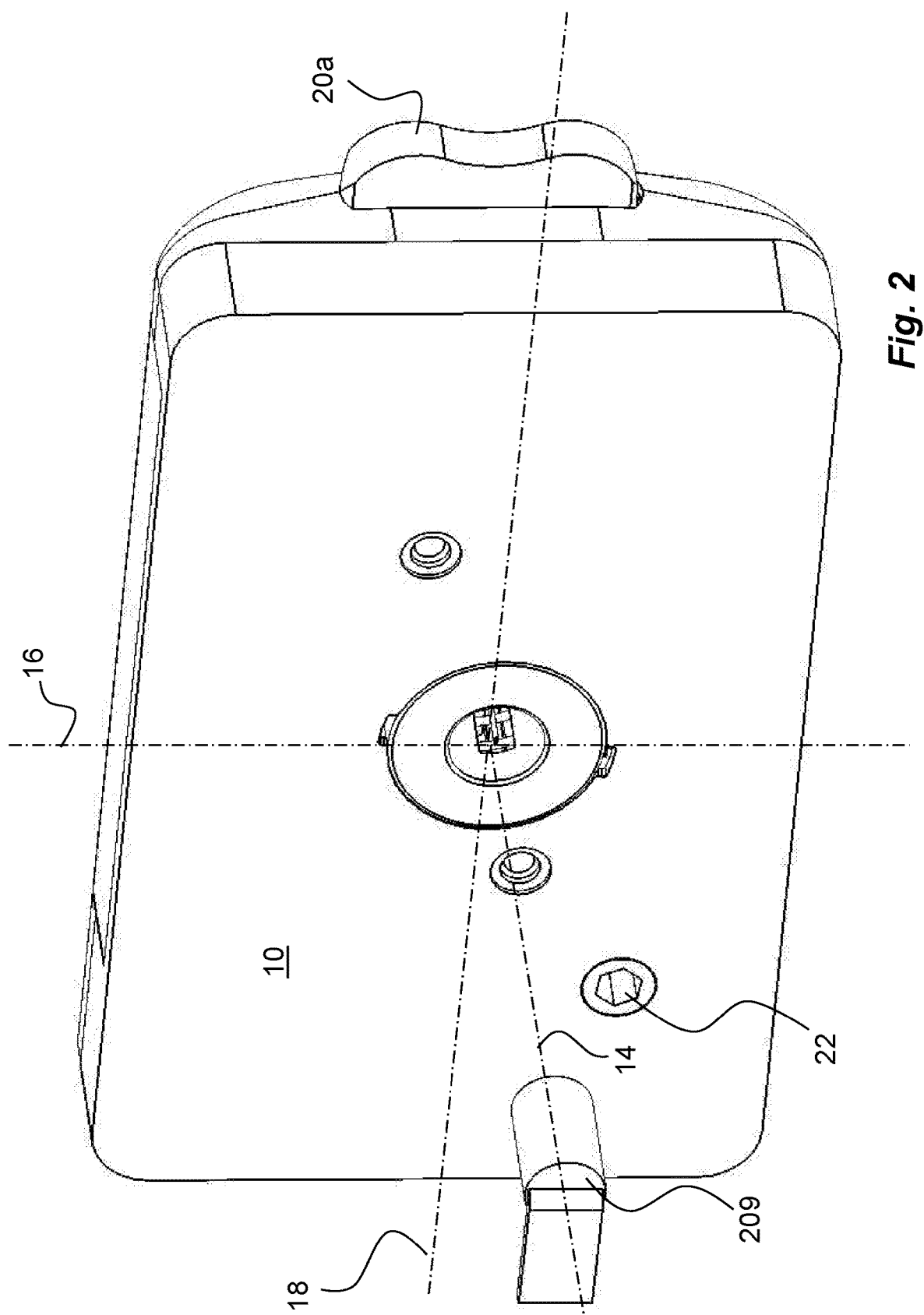
FIG. 2 is a perspective view of the device of FIG. 1 turned 180 degrees.

The embodiment of a medicament delivery device shown in the drawings comprises a housing, which may be in two housing parts 10, 12, FIGS. 1 and 2. It is of course feasible that it comprises more than two housing parts. Preferably, the complete housing has a generally rectangular shape having a measure or thickness as seen along a proximal-distal axis 14 that is much less than the dimensions in the other two directions, vertical 16 and horizontal 18. The housing is arranged with operating elements, 20a, b in the embodiment shown, FIGS. 1 and 2, as two buttons arranged on opposite side surfaces of the device.

The device is arranged with a driver 50, the function of which will be explained below. The driver comprises a shaft 24, FIG. 5, which shaft is rotatably arranged inside the housing and journalled with a distal end in a seat 26, FIG. 6, on the inner surface of the distal housing part 12. An Allen keyhole 22 is arranged on an end surface of a shaft 24, where the Allen keyhole 22 is accessible via an opening on the proximally directed housing surface, FIG. 2. A proximal end of the shaft 24 is arranged with a number of arms 28, FIG. 5, that extend in a generally circumferential direction. The free ends of the arms 28 are arranged with radially outwardly directed edges 30. The proximal end of the shaft 24 with the arms 28 is intended to fit into a seat 32, FIG. 7, on the inner surface of the proximal housing part 10. The seat 32 is surrounded by an annular ledge 34 having radially inwardly directed teeth 36 of a certain configuration. The teeth 36 are intended to cooperate with the free ends of the arms 28 as will be described.

Figure 4:
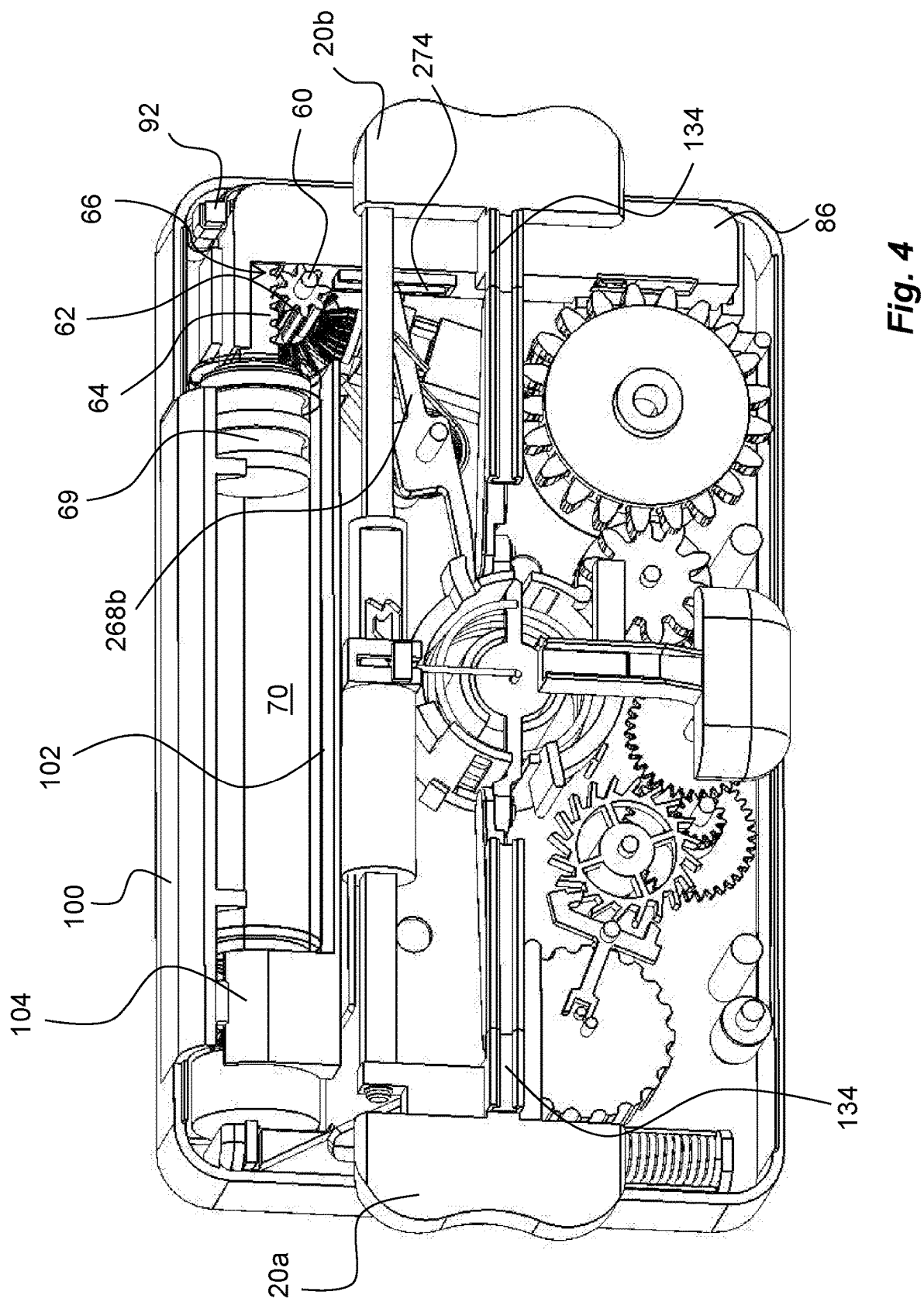
FIG. 4 is a perspective view of the device of FIG. 1 turned 180 degrees in relation to FIG. 3 and with a housing part removed.
Figure 5:
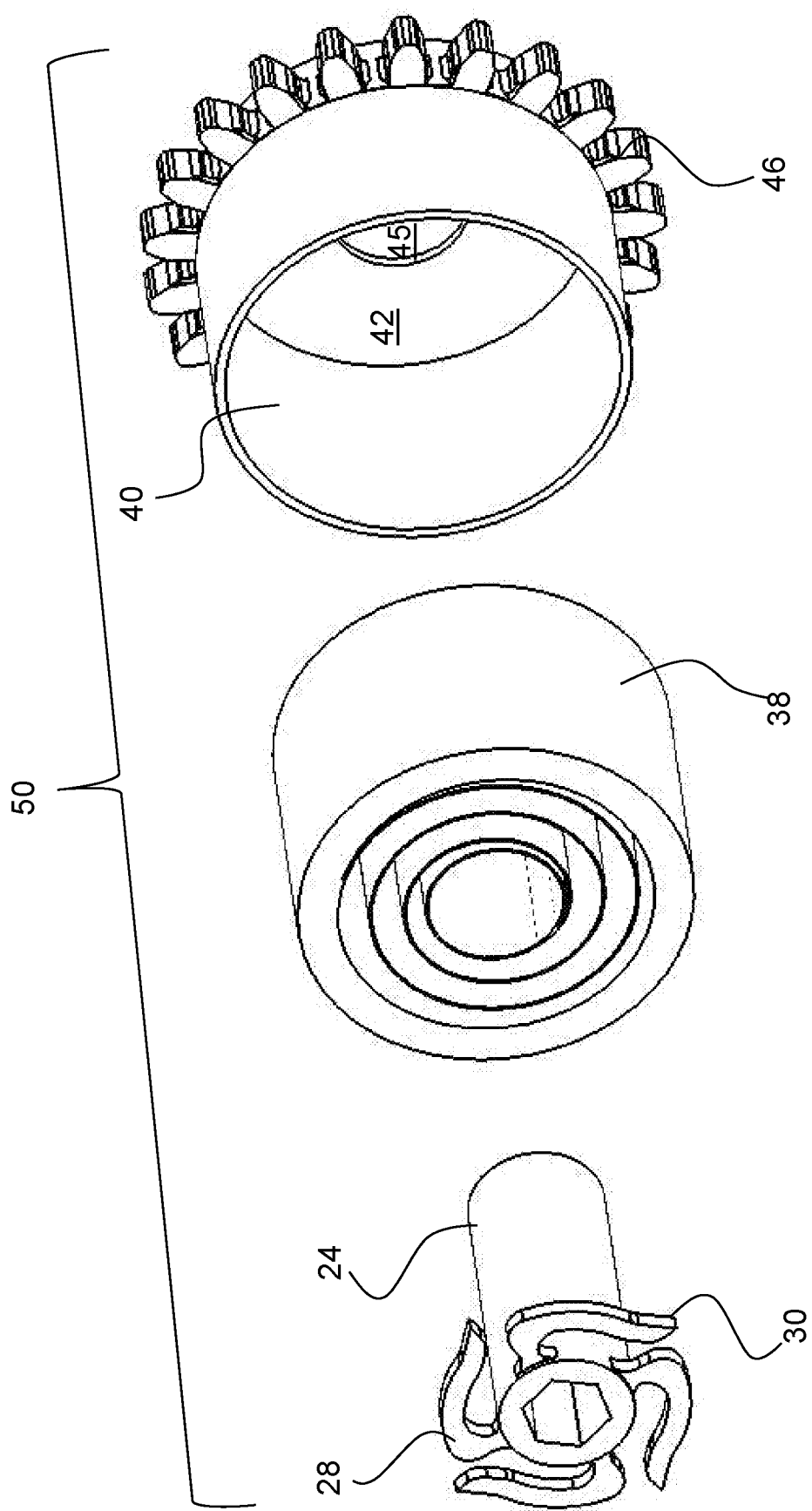
FIGS. 5-7 are detailed views of components and mechanisms comprised in the device of FIG. 1, FIGS. 8*a* and 8*b* show two different views of the same specific components and mechanisms of the device of FIG. 1.
Figure 6:
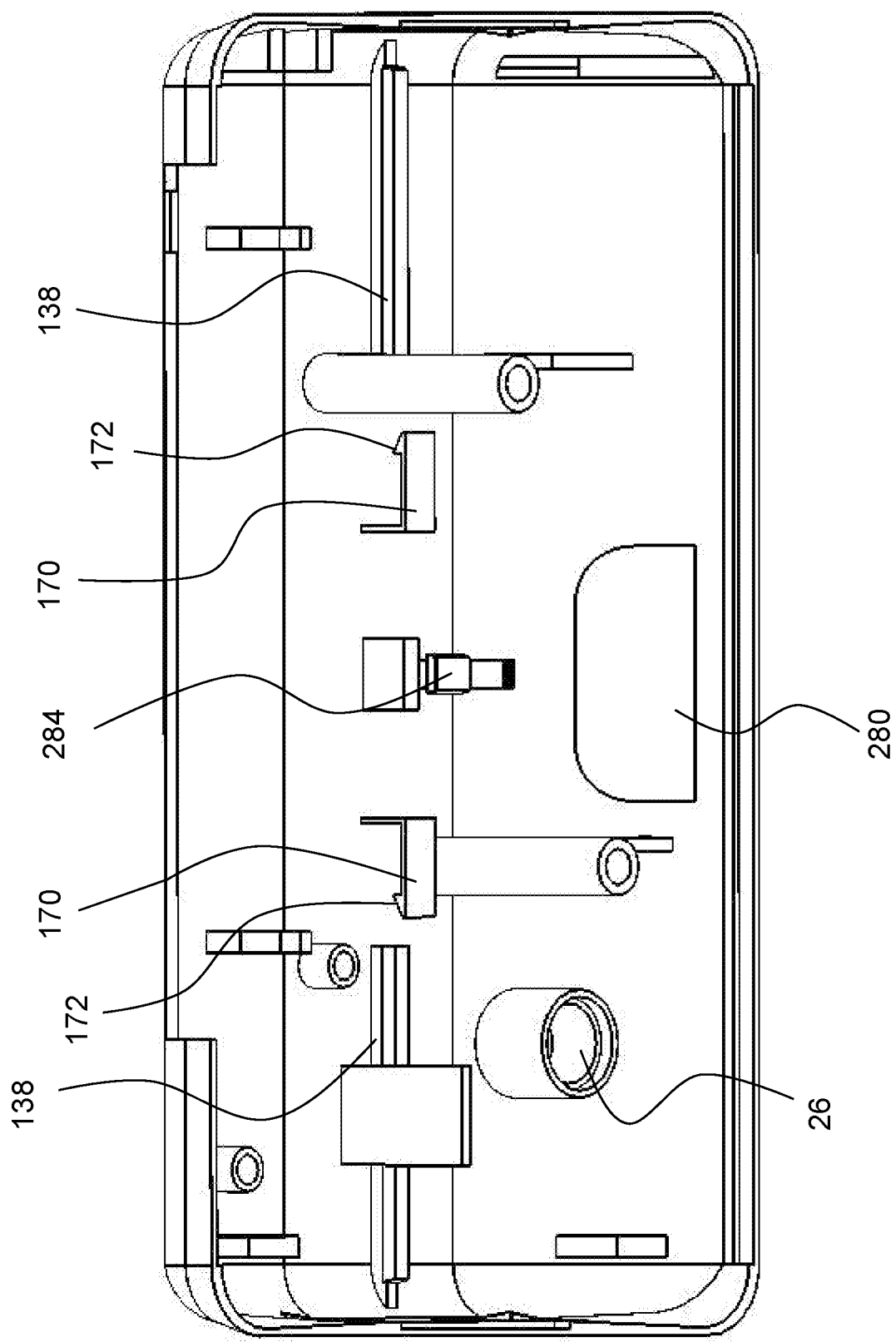
Figure 7:
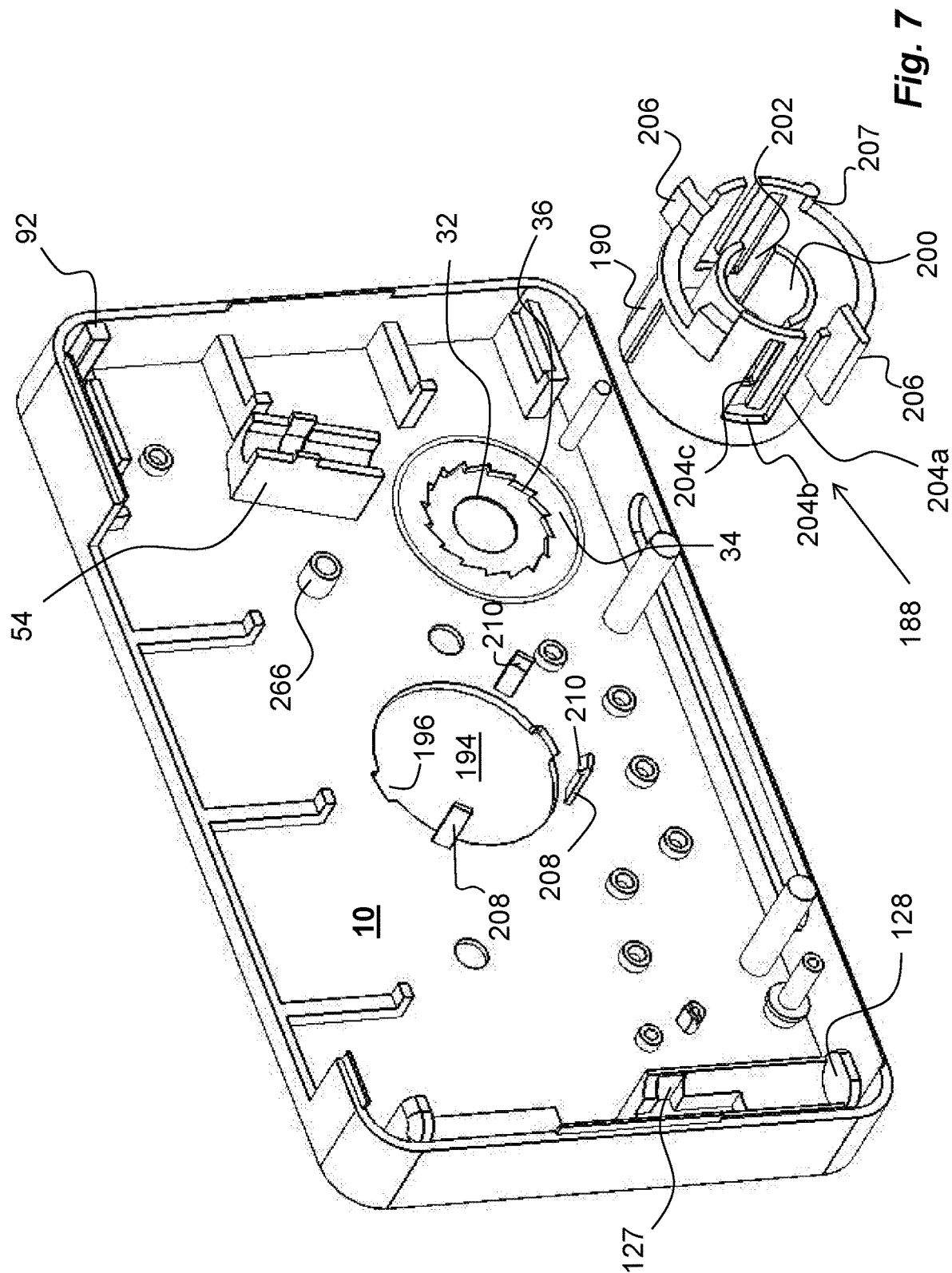
Figures 8A, 8B:
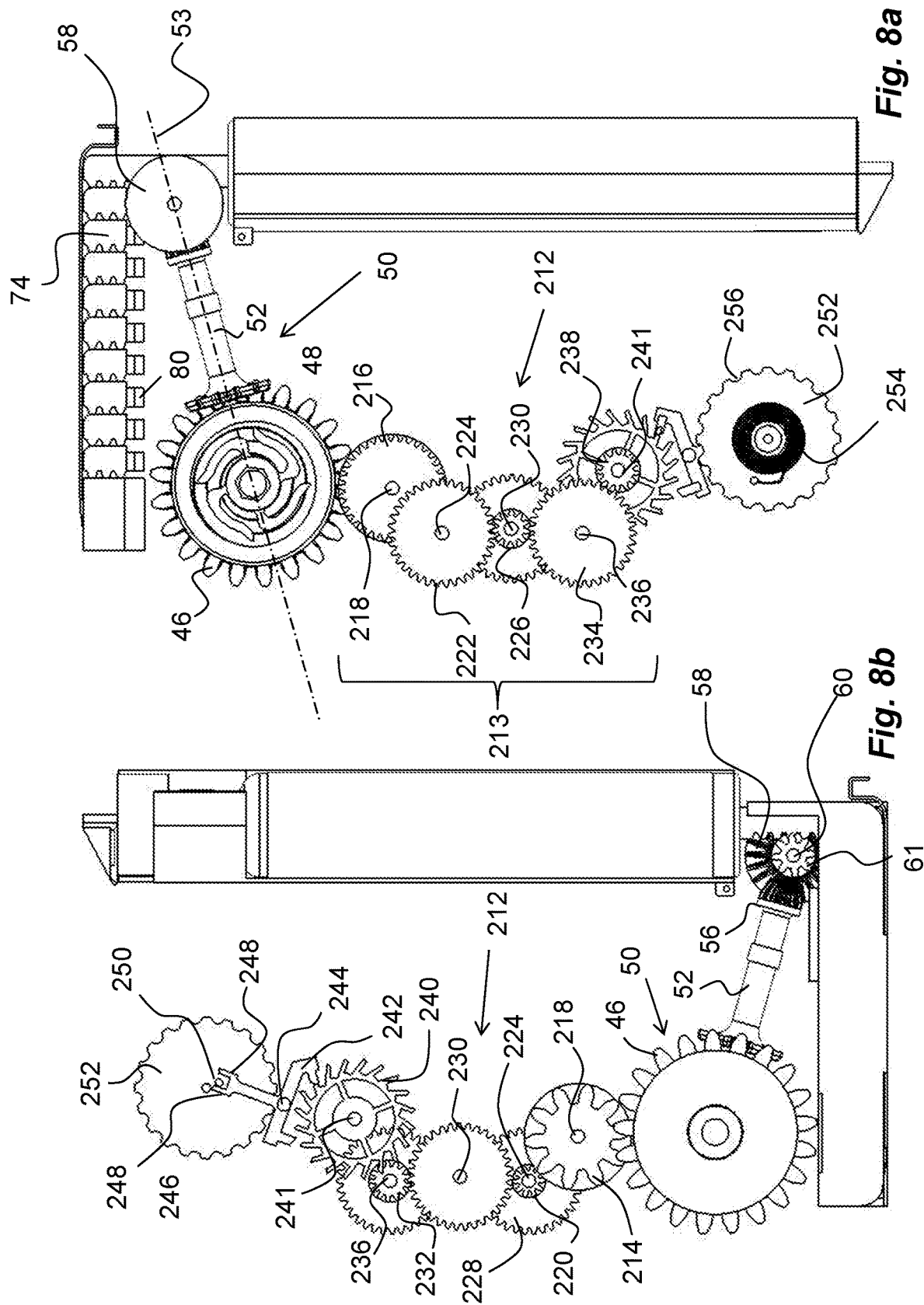

The driver 50 further comprises a flat spiral clock spring 38, FIG. 5, wound around the shaft 24, wherein an inner end of the spiral clock spring 38 is attached to the shaft 24. The spring 38 is further arranged inside a spring housing 40, FIG. 5, designed as a generally tubular part. An outer end of the spiral clock spring 38 is attached to an inner surface of the spring housing 40. The spring housing 40 is further arranged with a sidewall 42, FIG. 5, having a central opening 44, through which the shaft 24 can extend. On the outer circumferential surface of the spring housing 40 a ratchet 46 is arranged, FIG. 5. The ratchet 46 is intended to cooperate with a cogwheel 48 of the driver 50, FIG. 8. The driver 50 further comprises a shaft 52 where the cogwheel 48 is attached to one end such that the shaft 52 extends generally in the radial direction of the spring housing 40 as seen in FIG. 8 along line 53. The shaft 52 of the driver 50 is journalled in the proximal housing part 10 by support elements 54, FIG. 7. A second cogwheel 56, FIG. 8b, is attached to the second end of the shaft 52, having a generally conical shape. The second cogwheel 56 is arranged to be in contact with teeth of a third mating cogwheel 58. The third mating cogwheel 58 is journalled on a shaft 60 having an extension generally perpendicular to the extension of the shaft 52. Attached to the third mating cogwheel 58, or made integral with, is a drive wheel 61 having teeth 62 around its circumference. These teeth 62 are arranged to cooperate with corresponding teeth 64 on a plunger rod 66, FIG. 4.

In the embodiment shown the plunger rod 66 is of a certain configuration, FIGS. 9 and 10. The plunger rod 66 generally has a rectangular configuration as seen in a cross-sectional view. Further the plunger rod 66 is divided up into a number of plunger rod segments. The end of the first plunger rod segment 68 that is to be in contact with a stopper 69 of a medicament container 70, FIG. 4, is arranged with a generally circular pusher plate 72, FIG. 9, having a diameter somewhat less than the inner diameter of the medicament container 70. The first plunger rod segment 68 has a certain length. The following plunger rod segments 74, FIG. 9, are somewhat shorter. All plunger rod segments 74 are arranged with connection elements that comprise generally vertically arranged cut-outs 76 at their distal ends, FIG. 10. The sidewalls of the cut-outs 76 are arranged with generally vertically directed grooves 78, FIG. 10, having a certain configuration. Further, each plunger rod segment apart from the first segment, is arranged with a proximally directed nose 80 designed to fit into the cut-out 76 of a previous plunger segment 68. Further the nose 80 is arranged with generally vertically extending ledges 82 having similar configuration as the grooves 78 of the cut-out 76, whereby the ledges 82 may fit into the grooves 78. Further, the cut-outs 76 are arranged with flexible tongues 84, FIG. 10b that engage a surface of the nose 80 of a subsequent plunger rod segment so as to lock the segments to each other.

The plunger rod segments 74 are arranged in a generally vertical stack on top of each other and directed such that the nose 80 of the segments point in the same direction, FIGS. 8a and 9. The stack of plunger rod segments is held in place inside the housing by a magazine 86, FIG. 9 providing side supports on three sides. The fourth side is arranged with an elongated slit 88, FIG. 9. In the slit 88 a flat band spring 90 is arranged having a first upper end attached to a fixture post 92 on the proximal housing part 10, FIGS. 4 and 7. The second lower end of the band spring 90 is arranged with a coil 94, FIG. 9, which coil 94 fits into a cavity 96 attached to a plunger rod follower 98 positioned inside the magazine 86, FIG. 9. The function of the described components will be explained below.

Figure 3:
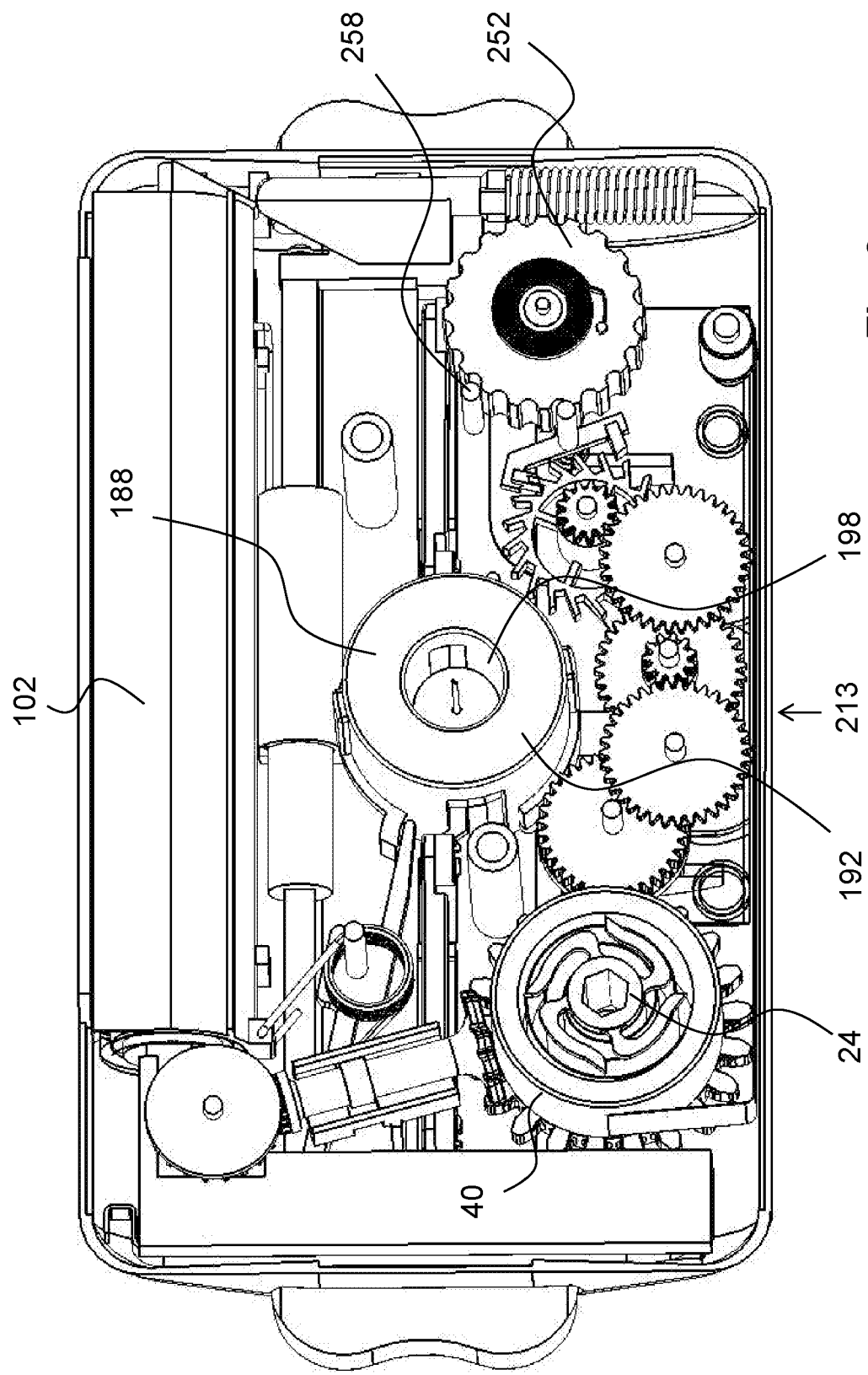
FIG. 3 is a perspective view of the device of FIG. 1 with a housing part removed.
Figure 11:
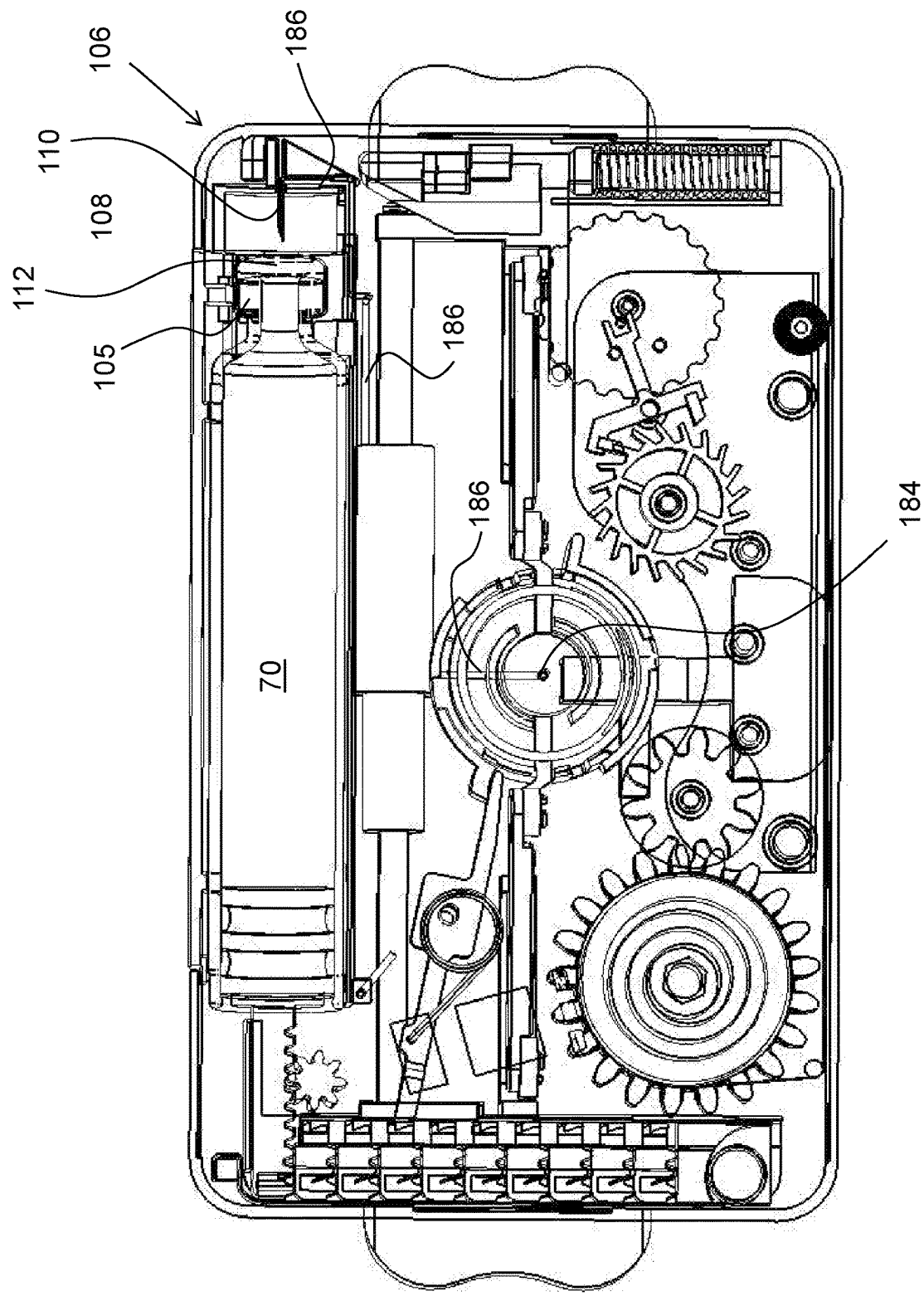

The proximal end of the plunger rod 66 extends into a space in the device intended to accommodate the medicament container 70, FIG. 4. The space is accessible via a hingedly attached lid 100, FIGS. 1 and 4, on an upper area of the housing. Inside the space a holder or cartridge retainer 102, FIGS. 3 and 4, is arranged, on which the medicament container 70 may be placed. In that respect, the cartridge retainer is arranged with a holding portion 104, FIG. 4, in which a neck portion 105, FIG. 11, of the medicament container 70 fits. A penetration mechanism 106 is further arranged in the device. It comprises a cup-shaped element 108, FIG. 11, arranged slidable in relation to the holding portion 104 and thus the neck portion 105 of the medicament container as seen in a longitudinal direction thereof. The cup-shaped element 108 is arranged with a hollow needle or a hollow pointed spike 110 directed towards the neck of the medicament container, FIG. 11, intended for piercing a septum 112 of the neck portion 105 of the medicament container 70.

Figure 12:
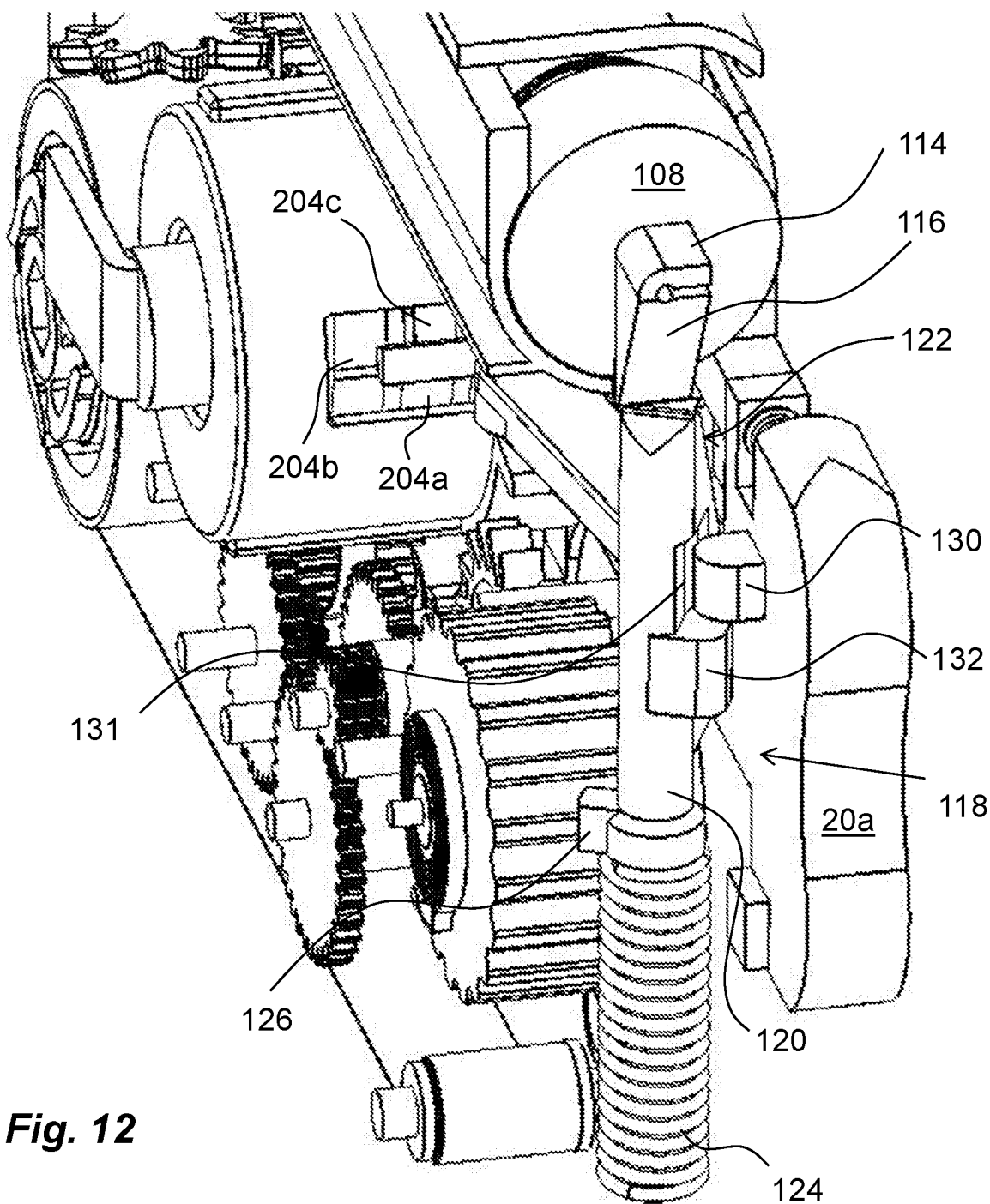

Further, an end surface of the cup-shaped element 108 is arranged with a ledge 114 having an inclined surface 116, FIG. 12. The ledge 114 is intended to interact with a pusher 118 of the penetration mechanism. The pusher 118 is designed as a generally elongated rod 120 provided with an inclined surface 122, FIG. 12, arranged to be in contact with the inclined surface 116 of the cup-shaped element 108. The pusher 118 is further arranged with a compression spring 124 arranged surrounding the rod 120 and fitted between a generally radially directed ledge 126 of the rod and a seat 128 in the housing parts as seen in FIG. 7. Further, in an initial position as seen in FIG. 12, the pusher 118 with its inclined surface 122 is somewhat turned in relation to the inclined surface 116 of the cup-shaped element 108. In this position, the ledge 126 fits into a recess 127 in the seat 128, FIG. 7, thereby locking the pusher with spring 124 compressed. Further, a generally radially extending protrusion 132 is arranged on the rod of the pusher, below a surface area 131 on the side of the pusher 118, FIG. 12.

The device is further arranged with an activation mechanism 129, FIG. 13. It comprises the two operating elements 20*a* and 20*b* that in the embodiment shown are arranged as push buttons. The push button 20*a* is arranged with a protrusion 130 on its side surface, FIG. 12. This protrusion 130 is intended to interact with the surface area 131 as will be explained below. Further, the protrusion 130 is positioned such in relation to the protrusion 132 of the pusher that any movement of the pusher in the vertical direction is prevented even if the ledge 126 would unintentionally be moved out of the seat 128, which might occur if the device was shaken or dropped on a hard surface.

Each push button 20*a, b*, is arranged with a generally U-shaped guide element 134, FIGS. 4 and 13, where the free ends of the U's of the guide elements 134 are arranged with inwardly directed ledges 136, FIG. 14. These guide elements 134 are intended to interact with guide rails 138, FIG. 6, on an inner surface of the distal housing part 12. The guide rails 138 are arranged with a generally T-shaped cross section as seen in FIG. 14.

Further, one of the push buttons 20*b* is arranged with an elongated rod 140, FIG. 13. The end of the elongated rod 140 is arranged with a generally cylindrical body 142. The cylindrical body 142 is designed to fit into a tubular body 144, which also is attached to an elongated rod 146. The elongated rod 146 is journalled in a post 147 of the other push button 20*a*, FIG. 13, so as to allow rotational movement of the elongated rod 146 and the tubular body 144 in relation to the push button 20*a*.

Figure 16:
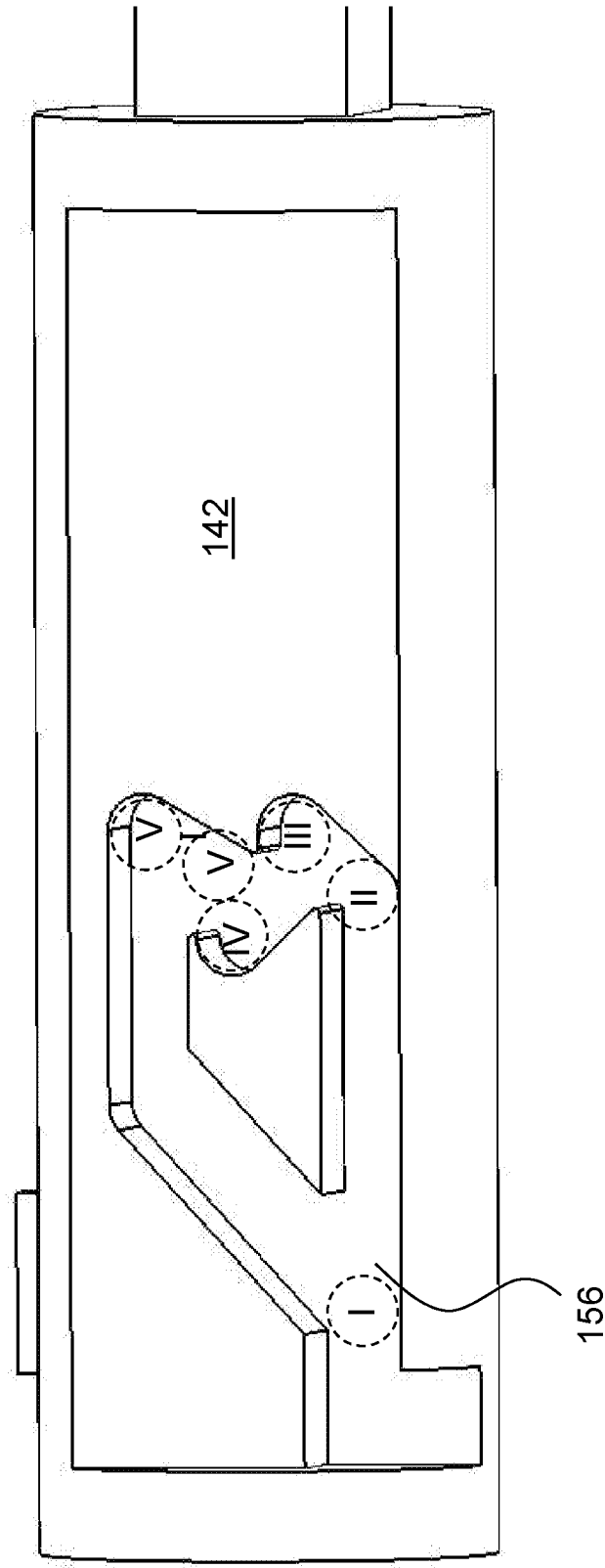
Figure 17:
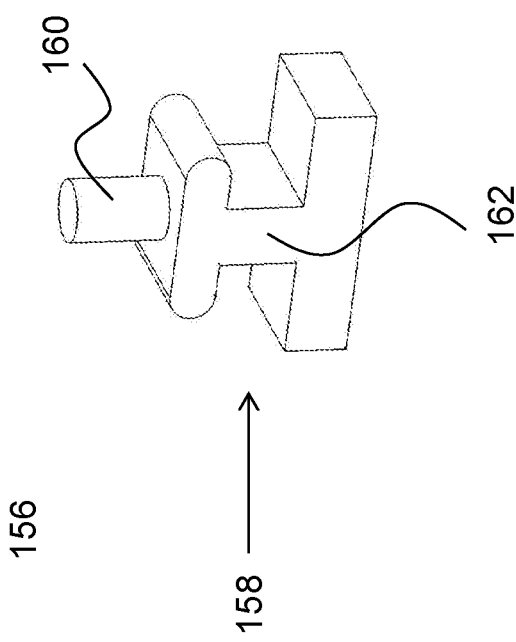

The cylindrical body 142 is further arranged with a ridge 148 extending in the longitudinal direction of the cylindrical body 142. The ridge 148 fits into a slit 150 in the tubular body 144, such that the bodies 142, 144 are rotationally locked to each other while allowing longitudinal movement between them. A compression spring 149, FIGS. 13 and 15, is arranged inside the tubular body 144 acting between an end wall 152 of the tubular body 144 and an end wall 154 of the cylindrical body 142. The cylindrical body is further arranged with grooves 156, FIGS. 15 and 16, having a certain configuration as will be described. A guide element 158, FIGS. 13 and 17, is arranged to be placed in the grooves with a pin 160. The pin 160 is attached to a generally T-shaped body 162, which body 162 fits into a slit 164 in the tubular body, which slit 164 is arranged generally perpendicular to the longitudinal direction of the tubular body 144, as seen in FIG. 13. These components form a pausing mechanism, as will be described.

Figure 18:
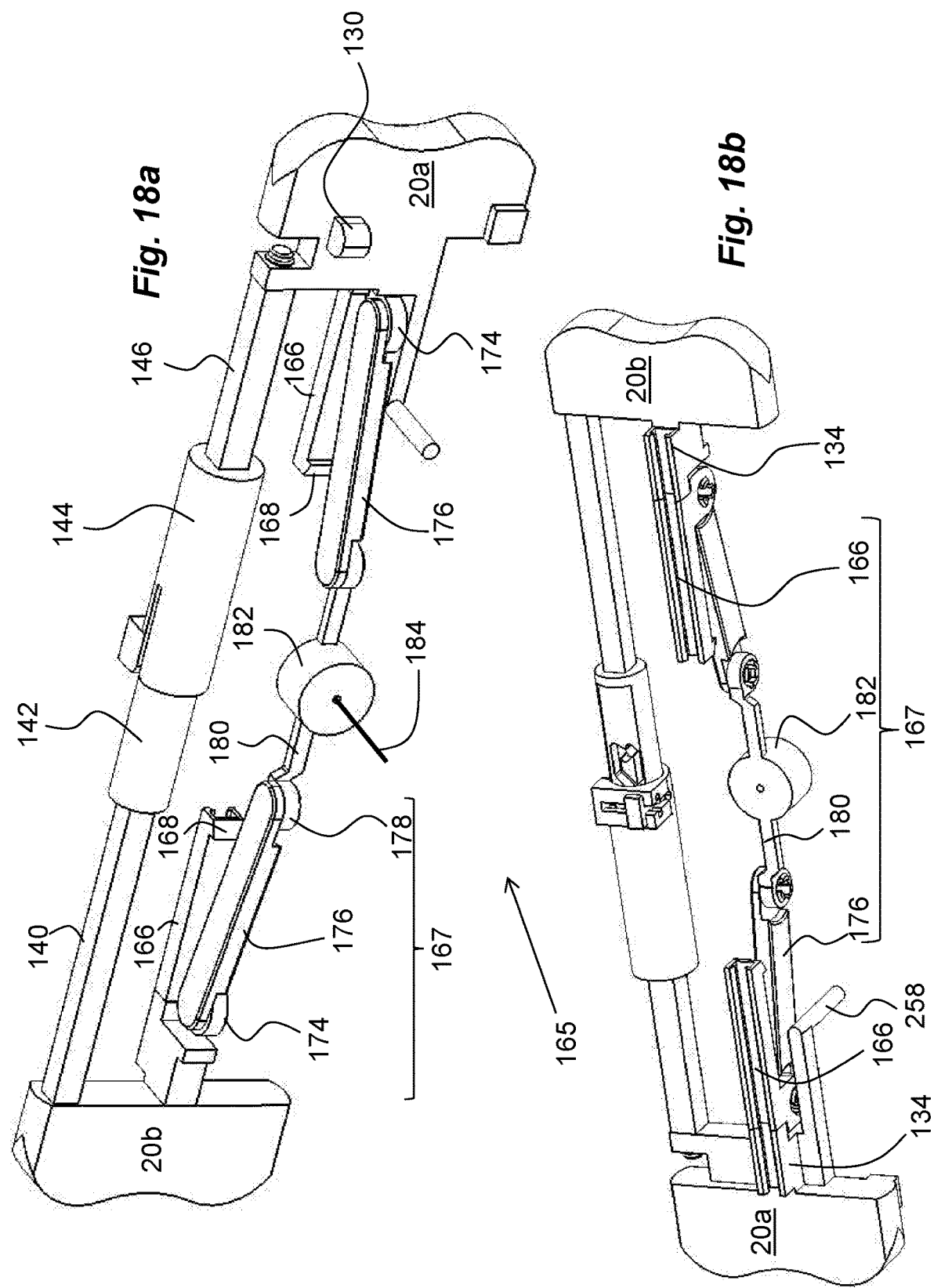
FIGS. 18a and 18b show two different views of the same specific components and mechanisms of the device of FIG. 1.

An actuation mechanism 165, FIG. 18, is further arranged to the activation mechanism. The actuation mechanism 165 comprises two elongated guide rods 166, FIG. 18, arranged slidable on the guide rails 138, FIG. 6. In that respect, the guide rods 166 preferably have the same shape as the guide elements 134 when seen in a cross-section. Each guide rod 166 is arranged with a ledge 168, FIG. 18*a*, extending generally transversal to the longitudinal direction of the guide rod 166. Each ledge 168 is designed to cooperate with a generally L-shaped holding element 170, FIG. 6, where the free end is arranged with a ledge 172 arranged to grip the transversal ledge 168 of the guide rod 166 as will be described.

A linkage 167 is comprised in the actuation mechanism, FIG. 18, wherein each guide rod 166 is further arranged with a first attachment post 174 comprising a bearing passage. A bearing shaft of an actuator arm 176 is journalled in the first attachment post 174. The opposite end of the actuator arm 176 is provided with a bearing shaft intended to fit into a bearing passage of a second attachment post 178. The second attachment post 178 is in turn attached to an arm 180 of a needle holder 182. The needle holder 182 is designed with a generally cylindrical outer shape. The needle holder is arranged with a central passage through which an injection needle 184 is extending. Further, a tube 186 is attached to one end of the injection needle 184, FIG. 11. The tube 186 then connects to the spike 110, thereby providing a passage between the spike 110 and the injection needle 184.

A needle cover 188 is further arranged to the device, FIGS. 3 and 7. It comprises a generally tubular body having a number of longitudinally extending ribs 190 on its outer surface, FIG. 7, in the embodiment shown two ribs 190 arranged on opposite sides of the needle cover 188. The ribs 190 end a short distance from a proximal end wall 192, FIG. 3, of the needle cover 188, which distance generally corresponds to the thickness of the proximal housing part 10. This is due to that the proximal end of the needle cover protrudes through a passage 194 in the proximal housing part, FIG. 7, where proximal end surfaces of the ribs 190 abut the inner surface of the proximal housing part 10 adjacent the passage 194.

The passage 194 is further arranged with cut-outs 196, FIG. 7, having generally the same shape as the ribs 190 in a cross-sectional view. The proximal end wall 192 of the needle cover 188 is further arranged with a central passage 198, FIGS. 3 and 19, which central passage 198 is surrounded by a generally tubular element 200, FIGS. 7 and 19, extending in the distal direction. The tubular element 200 has a diameter somewhat larger than the outer diameter of the needle holder 182, where the latter is able to slide inside the tubular part along the proximal-distal axis 14. The tubular element 200 is further arranged with two slits 202, FIG. 7, in which the arms 180 of the needle holder 182 may be positioned.

Figure 19:
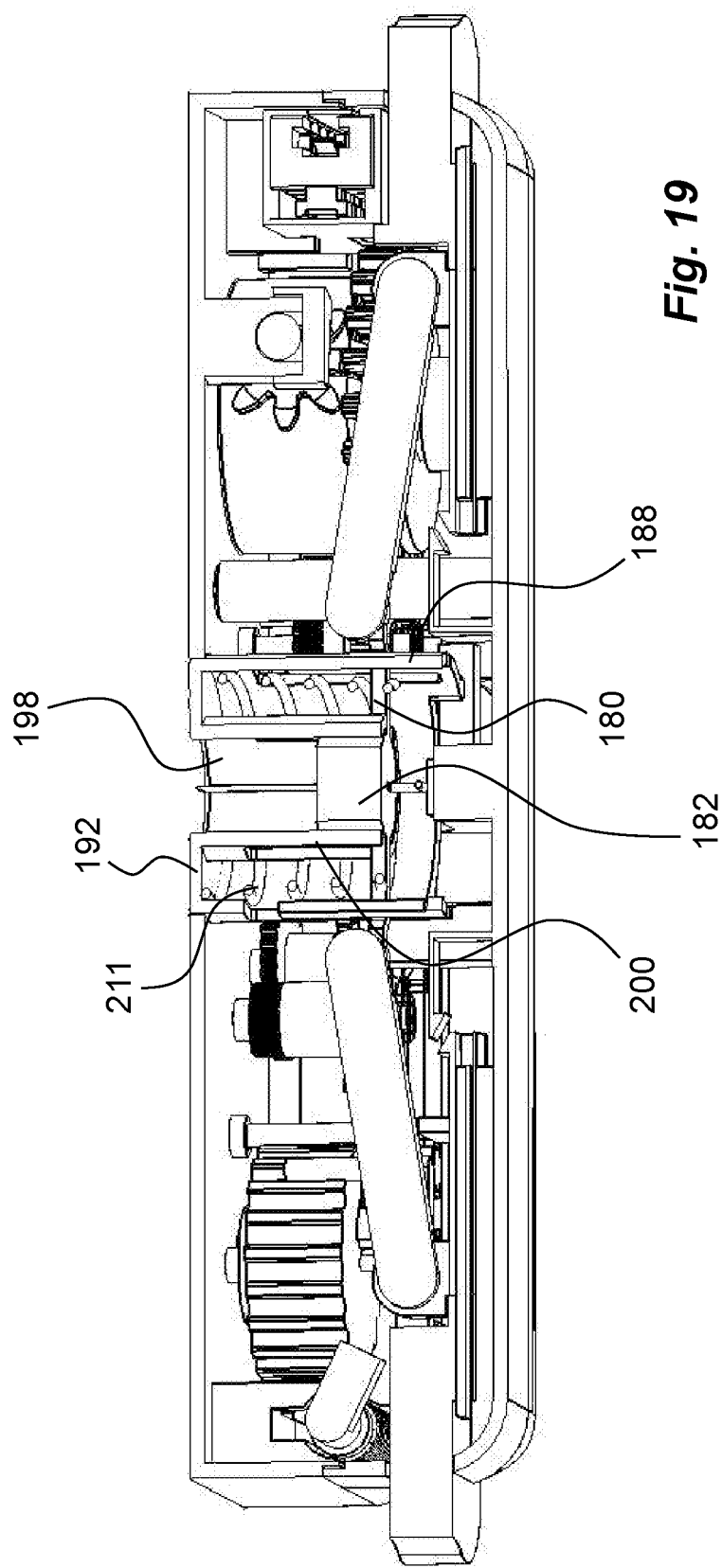
FIGS. 19-28 show different functional positions of the device during use.

Further the needle cover 188 is also arranged with slits 204, with a first part 204*a* open in the distal direction, where the first part 204*a* transforms into a second generally circumferential second part 204*b*, which in turn transforms into a third part 204*c* generally parallel with the first part 204*a* but closed in the distal end. The needle cover 188 is further arranged with radially outwardly extending ledges 206, FIG. 7, one on each side of the needle cover 188 as seen in the transversal direction. Further, a longitudinally extending ledge 207, FIG. 7 is provided in the distal end surface of the needle cover 188. Arms 208 are further arranged on the inner surface of the proximal housing part surrounding the passage extending in the distal direction, FIG. 7. These arms are arranged with radially inwardly extending ledges 210. Further, a needle cover spring 211, FIG. 19, is arranged between the inner surface of the end wall 192 of the needle cover 188 and the arms 180 of the needle holder 182. Also, a needle cap 209, FIG. 2, is releasibly arranged in the central passage 198 of the needle cover 188, surrounding the needle and keeping it sterile.

The device is further arranged with an injection speed control mechanism 212, FIG. 8, that preferably is capable of providing a constant injection speed during the injection. It comprises a transmission 213, FIGS. 8a and 8b, with a first cogwheel 214, FIG. 8b, acting on the ratchet 46 on the outer surface of the spring housing 40, where the first cogwheel 214 has a smaller diameter than the ratchet 46. The first cogwheel 214 is attached to a second cogwheel 216 having a diameter generally corresponding to the first cogwheel but with a larger number of teeth, wherein the first and second cogwheels 214, 216 are rotatably arranged to a first shaft 218. The second cogwheel 216 is in engagement with a third cogwheel 220 having a smaller diameter. The third cogwheel 220 is attached to a fourth cogwheel 222 having a larger diameter. The third and the fourth cogwheel 220, 222 are rotatably arranged to a second shaft 224.

The fourth cogwheel 222 is then in engagement with a fifth cogwheel 226 having a smaller diameter. The fifth cogwheel 226 is attached to a sixth cogwheel 228 having a larger diameter. The fifth and the sixth cogwheels 226, 228 are rotatably arranged to a third shaft 230. The sixth cogwheel 228 is in engagement with a seventh cogwheel 232. The seventh cogwheel 232 is attached to an eighth cogwheel 234. The seventh and eighth cogwheels 232, 234 are arranged on a fourth shaft 236. The eighth cogwheel 234 is in engagement with a ninth cogwheel 238. The ninth cogwheel is attached to an escapement wheel 240 having a number of teeth. The ninth cogwheel 238 and the escapement wheel 240 are arranged on a fifth shaft 241.

A pallet fork 242 is arranged rotatable on a shaft 244 where the arms of the fork are arranged to act on the teeth of the escapement wheel 240. Further an arm 246 is arranged to the pallet fork 242 where the free end of the arm 246 is arranged with two fingers 248. These fingers are in engagement with a protrusion 250 attached on a side surface of a regulator wheel 252. One end of a balance spring 254 is attached to the regulator wheel 252 and the other end of the balance spring 254 is attached to a housing part of the device, capable of oscillating said regulator wheel when activated.

The outer circumferential surface of the regulator wheel 252 is arranged with indentations 256. The protrusion 250 of the regulator wheel 252 is positioned such in relation to the fingers 248 that oscillation of the regulator wheel 252 will cause the pallet fork 242 to swing back and forth. A more detailed function will follow below. A locking element 258 in the form of an arm attached to the push button 20a, FIGS. 3 and 13, is arranged to fit into the indentations 256 in an initial position of the push button 20a, as will be explained below.

Figure 20:
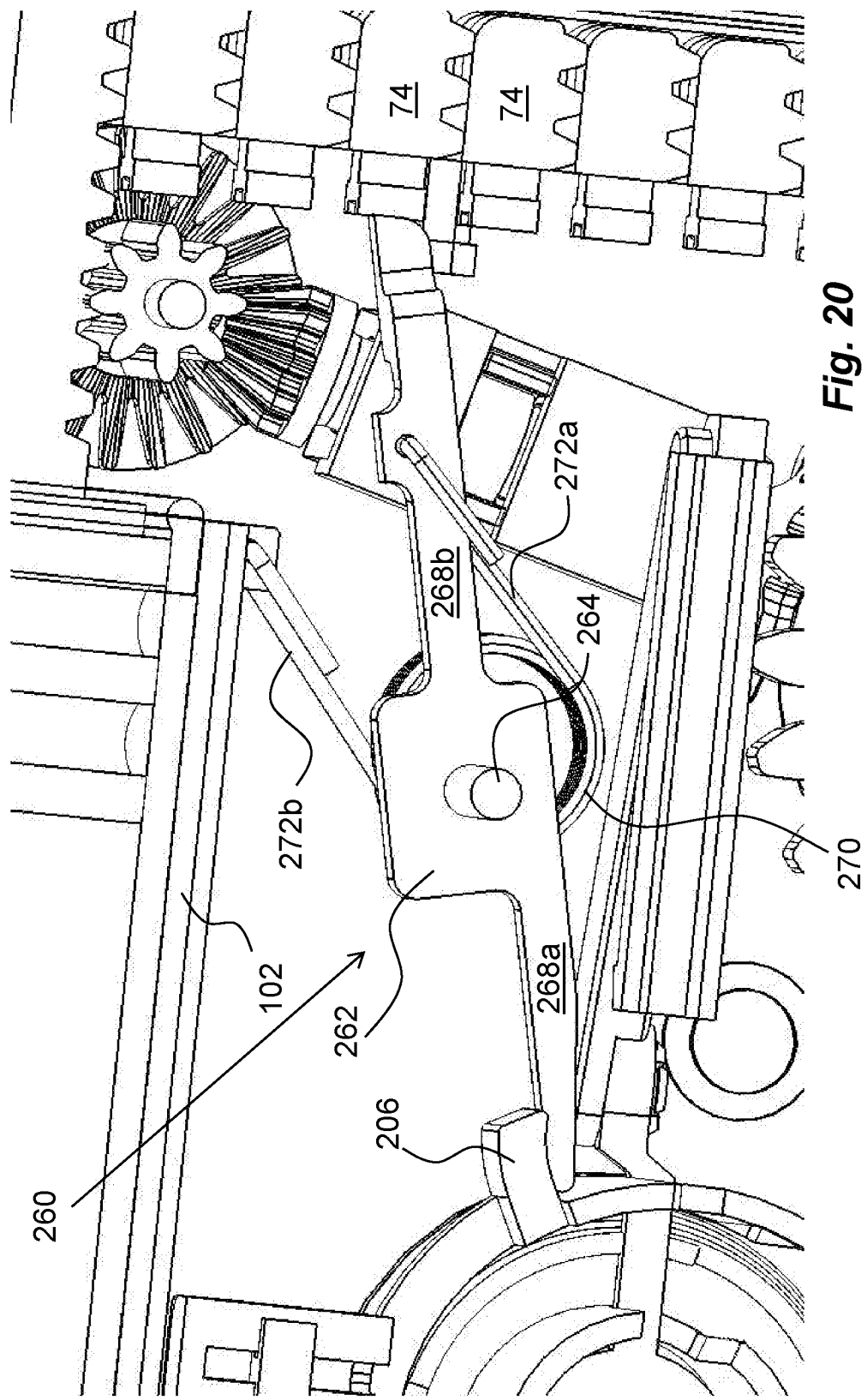

The device is further arranged with an auto-stop mechanism 260, FIG. 20. It comprises a beam 262 arranged with a shaft 264 journalled in a post 266 on an inner surface of the proximal housing part 10, FIG. 7. The shaft 264 is positioned generally midway along the longitudinal direction of the beam, producing two oppositely directed first and second arms 268a, 268b. An end of the first arm 268a is arranged to be in contact with one of the ledges 206 on the needle cover 188, as seen in FIG. 20. A torsion spring 270 is further wound around the post 266 and is attached with one free end 272a to the second arm 268b of the beam. The other free end 272b of the torsion spring 270 is attached to a fixed housing part, in the embodiment shown the cartridge retainer 102. The second arm 268b extends through an opening 274 in the magazine 86, FIG. 4, having a free end that is in contact with and pushes against the plunger rod segments 74 due to the force of the torsion spring 270, as seen in FIG. 20.

Figure 21:
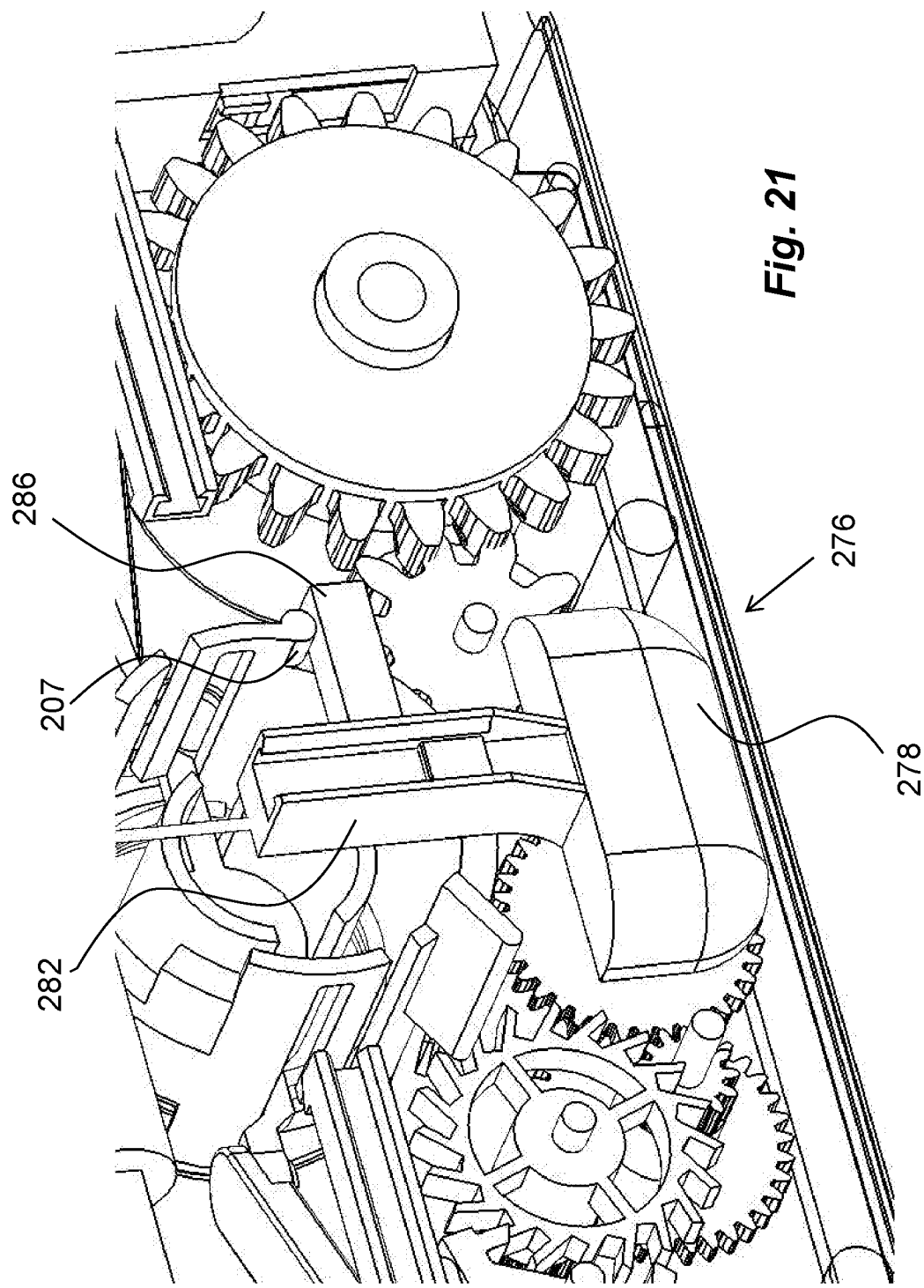

The device is further arranged with a manually operated stop mechanism 276, FIG. 21. It comprises an actuator element 278 in the form of a button that is accessible via an opening 280 in the distal housing part, FIG. 6. The actuator element 278 is arranged with an arm 282 having a generally U-shaped form as seen in cross-section. The free ends of the U are arranged with inwardly directed ledges. A guide post 284, FIG. 6, attached to the inner surface of the distal housing part, is arranged to fit inside the U-shaped arm, providing guiding action of the stop mechanism when moved linearly as will be described. The stop mechanism 276 further comprises a beam 286 FIG. 21, directed generally transversal to the arm 282. In an initial position of the stop mechanism, an upper surface of the arm 282 is in contact with the ledge 207 of the needle cover 188 as seen in FIG. 21.

Intended Function of the Device

The device is usually delivered without a medicament container. Thus, before use, a medicament container 70 has to be inserted into the device. The lid 100 at the upper end of the device is then opened, whereby the space and the cartridge retainer 102 are accessible. The medicament container 70 is then inserted with a neck portion towards the holding portion 104 of the cartridge retainer 102. The lid is then closed.

The device is now made ready. This may be done by inserting an Allen key into the hole 22 on the proximal surface of the device and turning the shaft 24 in the clockwise direction. This in turn causes the arms 28 to slide over the teeth 36 because of the direction of the arms in relation to the teeth. Because the inner end of the spiral clock spring 38 is attached to the turning shaft 24 the spiral clock spring 38 is tensioned. When the user stops turning the shaft 24, it is locked against rotating back because of the edges 30 of the arms 28 now locking against the teeth 36. Also, after activation of the device, the shaft 24 cannot be rotated again. The device is now ready for delivering a dose of medicament.

In the initial position, the operating elements, the activation buttons 20a, 20b, are in their extended position as seen in FIGS. 3 and 4. In this position, the locking element 258 is in engagement with the regulator wheel 252, as seen in FIG. 3, whereby action of the constant speed control mechanism 144 is prevented. The balance spring 254 has been tensioned beforehand. The process up to this point may be done without the device being in contact with the patient. In order to be able to deliver a dose of medicament to the patient, the needle cap 209 is removed from the central passage 198 of the needle cover 188 and the proximal surface of the device has to be in contact with some part of the body of the patient, i.e. to releasibly attach the device to the body. This may be performed in many ways, by straps, by merely pressing it manually, but preferably the proximal surface is arranged with some sort of adhesive, like sticky tape, with which the device may be fastened to the body. One variant is to have double-sided sticky tape on the proximal surface with an outer protective layer that is peeled off before attachment.

Activation of the Device

When the device is to be activated, the user presses both activation buttons 20a, 20b towards each other. This causes several things to be initiated.

1. Connection of Medicament Container

When the activation button 20a is moved inwards, the protrusion 130 on the activation button is moved along the surface area 131 of the pusher, thereby turning the latter around its longitudinal axis. This causes the ledge 126 to be moved out of the locking engagement with the recess 127 out of contact with the protrusion 132 of the penetration mechanism. Also the protrusion 130 is moved away from the protrusions 132 of the pusher. Thus, the pusher 118 is released and is forced upwards due to the compression spring 124, FIG. 22. This causes the inclined surface 122 of the pusher 118 to be moved in contact with the inclined surface 116 of the ledge 114 of the cup-shaped element 108 such that cup-shaped element 108 and the spike 110 is moved towards the neck of the medicament container, which in turn causes the end of the spike 110 to penetrate the septum 112, creating a passage between the interior of the medicament container and the injection needle via the tube 186.

2. Penetration of Patient

Figure 23:
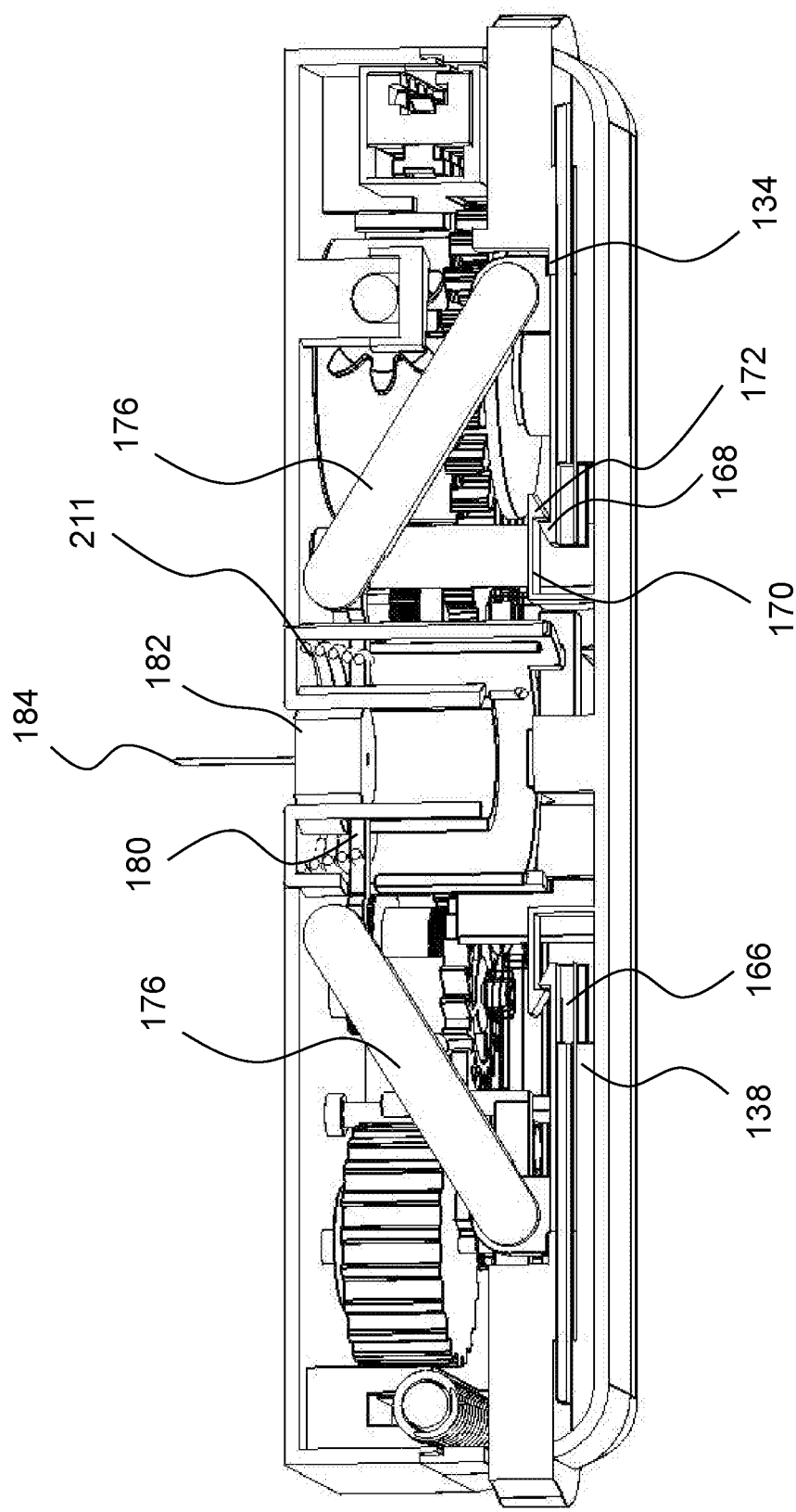

The inwards pressing of the activation buttons causes the guide elements 134 to move inwards along the guide rails 138. The guide elements 134 will thereby also move the guide rods 166 inwards, FIG. 23. Due to the attachment of the needle holder 182 with the guide rods 166 via the actuator arms 176, the needle holder 182 with its injection needle 184 will move in the proximal direction whereby the injection needle 184 will extend in the proximal direction beyond the surface of the proximal housing part, causing a penetration of the patient. The advancement of the needle holder 182 with its arms 180 will compress the needle cover spring 211, as seen in FIG. 23. When the guide rods 166 have advanced inwards a certain distance inwards, the ledges 168 of the guide rods 166 will pass the ledges 172 of the holding elements 170. This prevents the guide rods 166 from moving back outwards, and holds thus the needle holder with the injection needle in the extended position as seen in FIG. 23.

Also, when the activation buttons are pressed inwards, the cylindrical body 142 will move inside the tubular body 144, compressing the spring 149. The pin 160 of the guide element 158 will move in the grooves 156 on the outer surface of the cylindrical body as seen in FIG. 16 from a start position I. When the pin 160 reaches position II and follows the inclined surface of the groove to position III, the body 162 of the guide element will move in the slit 164. In this position, the activation buttons are in their most depressed position and the injection needle has penetrated the patient, who may now release the buttons. This will cause the pin 160 to move to position IV, keeping the activation buttons in a rather depressed state.

3. Start of Injection

Figure 22:
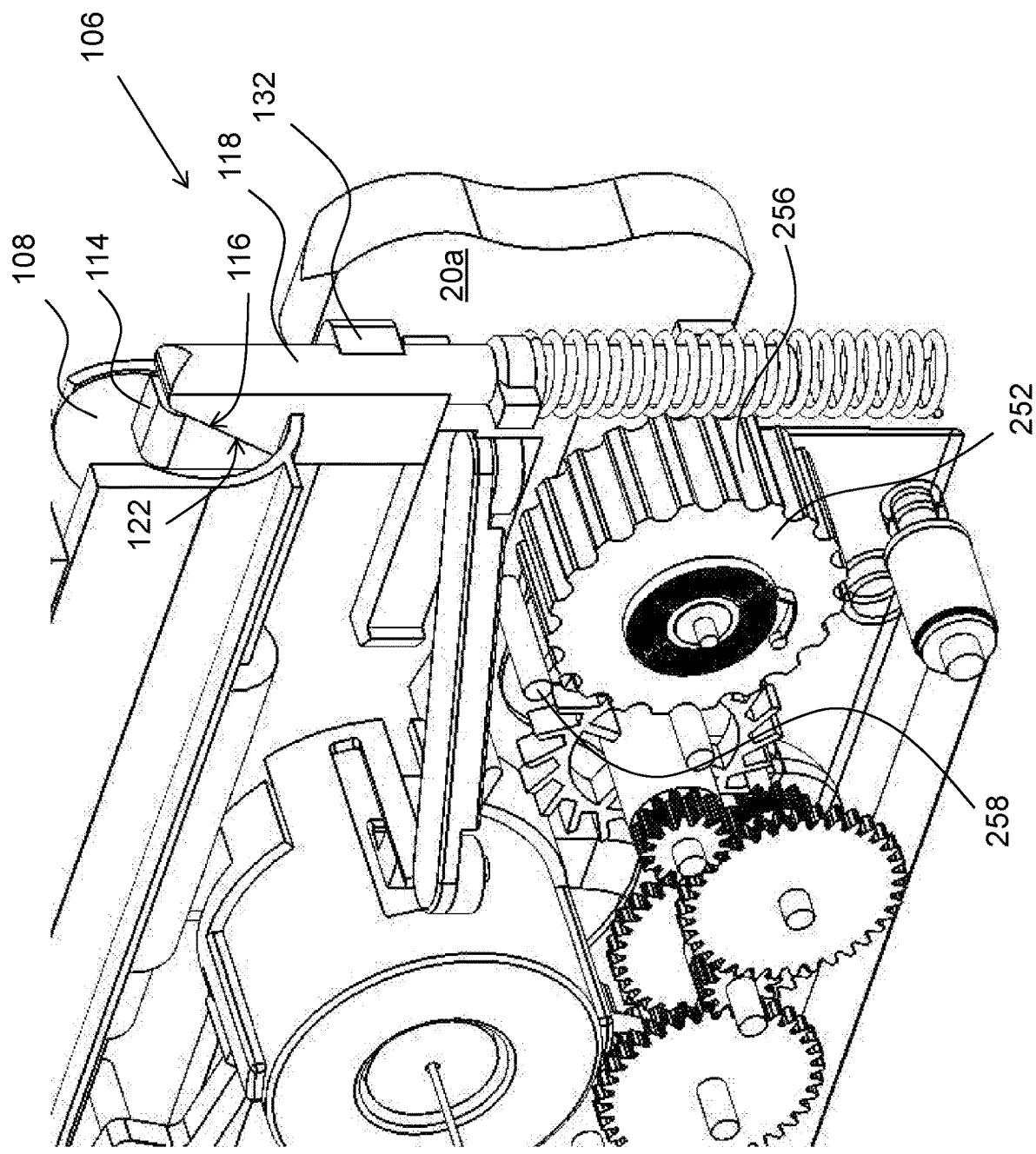

The inwards pressing of the activation buttons will also cause the injection to start in that the locking element 258 of the activation button 20*a* is moved out of contact with the indentations 256 of the regulator wheel 252, as seen in FIG. 22. The tensioned balance spring 254 will now oscillate the regulator wheel 252, whereby the pallet fork 242 will start to oscillate back and forth due to the contact with the protrusions 250 on the regulator wheel.

This in turn will cause the escapement wheel 240 to move an increment or rotational angle per time unit, thus controlling the speed. This rotational speed is then transferred through the transmission 213 to the spring housing 40, determining the rotational speed of the spring housing 40. However, it is the spiral clock spring 40 that causes the spring housing 40 of the driver 50 to rotate, the transmission merely regulates the rotational speed.

Injection Operation

The rotation of the spring housing 40 will cause its ratchet 46 to move around the circumference, thereby acting on the cogwheel 48 of the driver 50. Thus the shaft 52 will rotate as will the second conical cogwheel 56. The rotation of the conical cogwheel 56 is transferred to the third mating cogwheel and thus the drive wheel 61. Because the teeth 62 of the drive wheel 61 are in engagement with the teeth 64 of the first plunger rod segment 68, the first plunger rod segment 68 is moved in the direction of the medicament container 70, whereby the pusher plate 72 acts on the stopper 69 in the medicament container 70. When the first plunger rod segment 68 has moved a distance towards and inside the medicament container 70, the space behind the first plunger rod segment 68 is so large that a subsequent plunger rod segment 74 may be pushed in the vertical direction by the flat band spring 90 acting on the lowermost positioned plunger rod follower 98 in the magazine 86. When the following plunger rod segments 74 are pushed upwards in the vertical direction, they are connected to a previous plunger rod segment in that the ledges 82 of the nose 80 of the subsequent segment fit into the grooves 78 of the cut-out 76 of the previous segment and in that the plunger rod segments are inter-locked by the flexible tongues 84. In this manner a sequentially "building" of a continuous plunger rod 66 is performed with the segments while performing injection of medicament from the medicament container 70 through the injection needle 184 via the tube 186.

Pausing of the Injection

The user may pause the injection by pressing shortly at both activation buttons 20. This will cause the pin 160 of the pausing mechanism to be moved from position IV in FIG. 16 to position V and along the inclined surface to position VI, causing the body 162 to move further upwards in the slit 164. When the user releases the activation buttons, the spring 149 between the cylindrical body 142 and the tubular body 144 will force the buttons outwardly to the initial start position while the pin 160 also is moved back to the start position I along the walls of the groove as seen in FIG. 16. The return of the activation buttons to their initial positions will in turn bring the locking element 258 in engagement with the indentations 256 of the regulator wheel 252 such that the rotation of the regulator wheel 252 is stopped. This in turn stops the spring housing 40 from rotation via the transmission, whereby the injection is stopped.

The user may then resume the injection by pressing again on the activation buttons 20 *a, b*, whereby the locking element 258 is moved out of contact with the regulator wheel, and the sequence continues in the same manner as described above.

Auto-Stop Function

Figure 24:
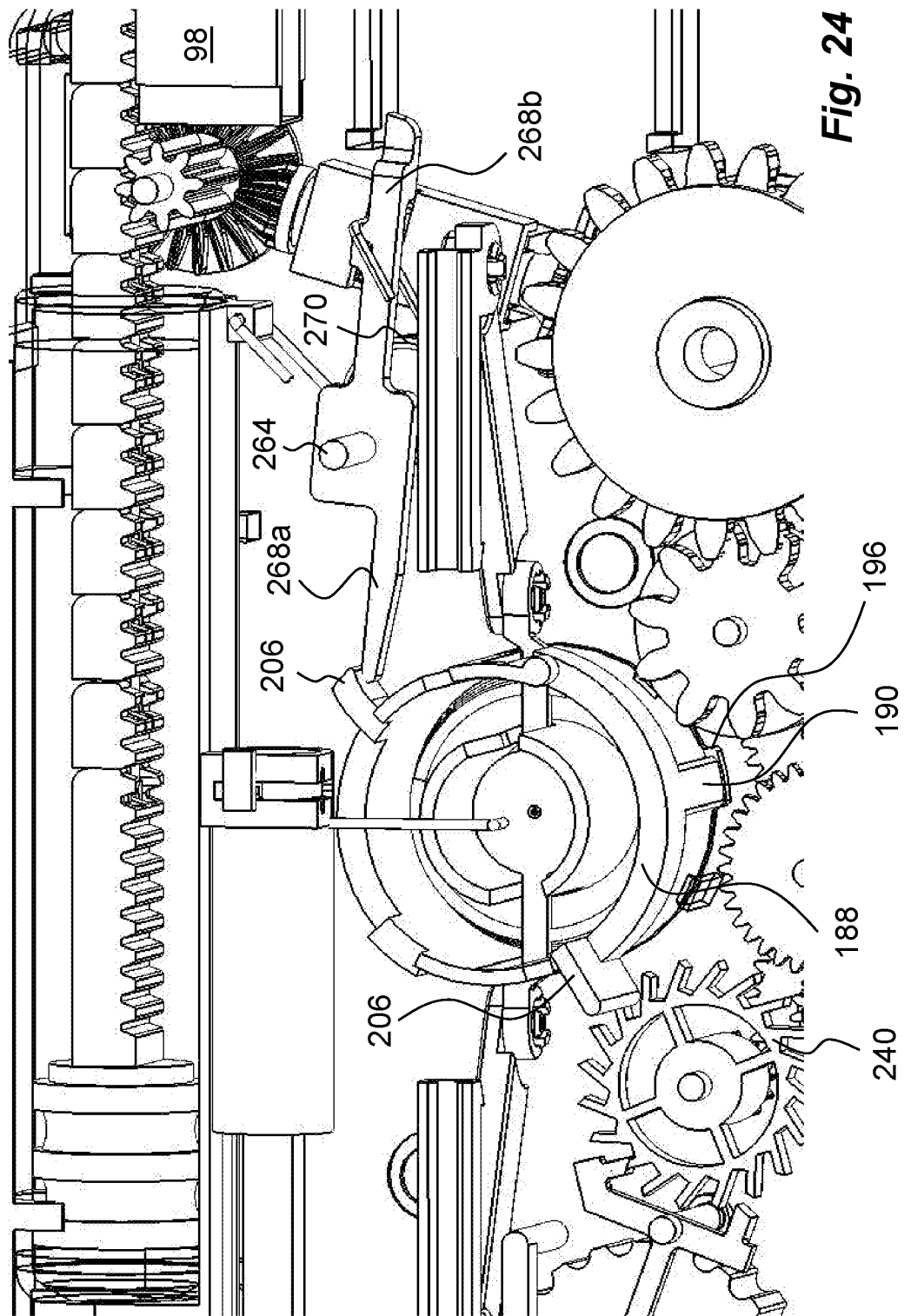

As described earlier, the second arm 268*b* of the auto-stop mechanism 260 is resting against the plunger rod segments 74 in the magazine. However, when the injection sequence is about to end when the medicament container has been emptied, there will be a space under the plunger rod follower 98, which has been moved upwards during the "building" of the plunger rod. Thus the second arm 268*b* is moved out of contact and the force of the torsion spring 270 will cause the beam 262 to turn around its shaft 264, whereby the first arm 268*a* will act on the ledge 206 of the needle cover 188, FIG. 24. This will in turn cause the needle cover 208 to be turned around its longitudinal axis, which coincides with the proximal-distal axis 14.

Figure 25:
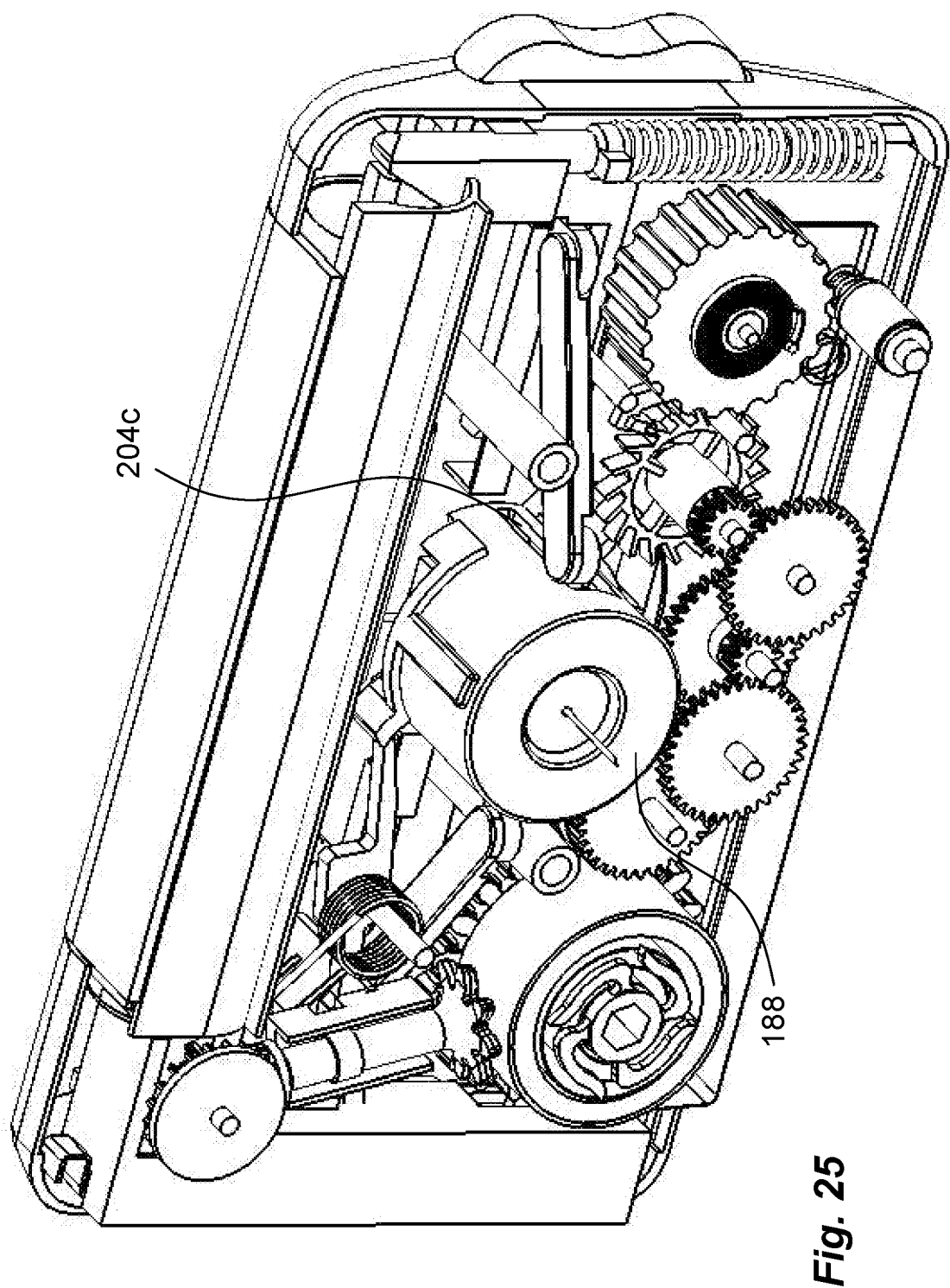
Figure 26:
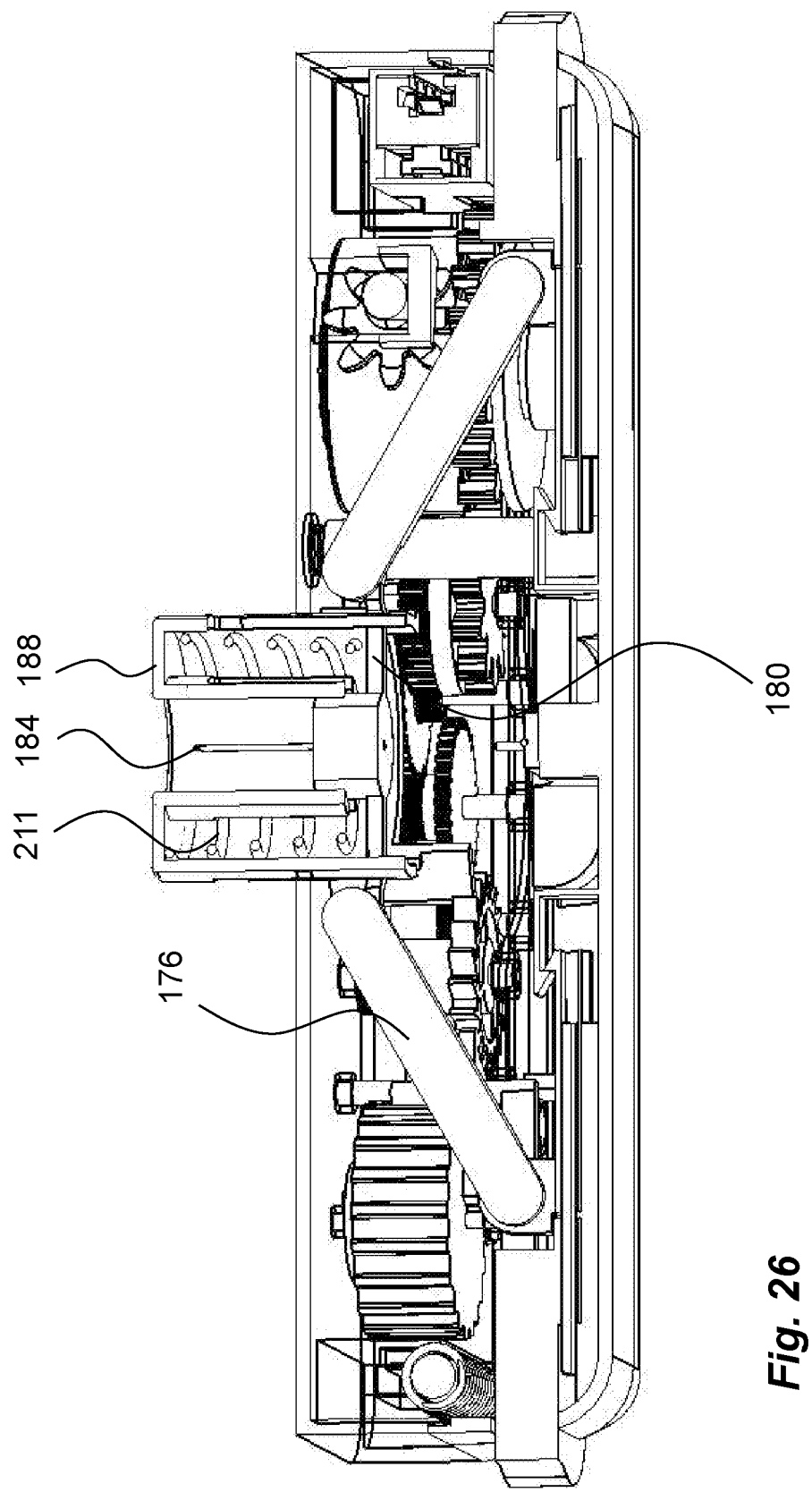
Figure 27:
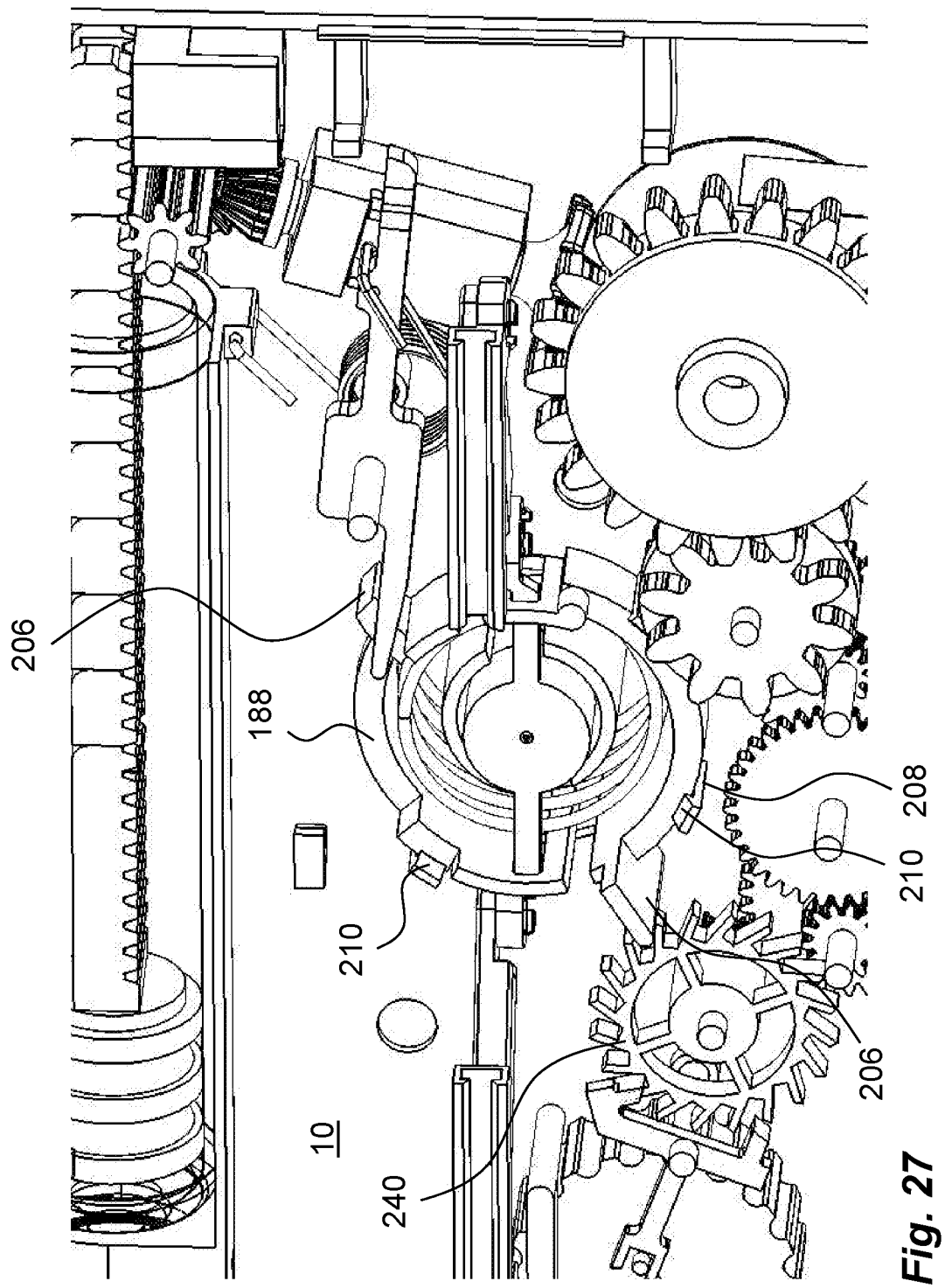

The turning of the needle cover 188 will further cause the arms 180 of the needle holder 182 to be moved from the first part 204*a* of the slit to the third part 204*c* of the slit via the second part 204b, FIGS. 12 and 25. The turning of the needle cover 188 will cause the ribs 190 on the outer surface of the needle cover to be aligned with the cut-outs 196, FIG. 24 and due to the force of the needle cover spring 211 the needle cover 188 is urged in the proximal direction. When now the device is removed from the body of the patient, the needle cover 188 will extend and surround the needle cover 188, FIG. 26. The movement of the needle cover 188 is stopped when the ledges 206 come in contact with the inner surface of the proximal housing part 10. When in this position, the ledges 210 of the arms 208 on the inner surface of the proximal housing part 10 will engage the distal end surface of the needle cover 188, preventing any movement of the needle cover 188 in the distal direction, thus locking the needle cover 188 in relation to the housing and the injection needle. Further, one of the ledges 206 is moved in contact with the teeth of the escapement wheel 240, FIG. 27, thereby preventing any further action or movement of the injection speed control mechanism 212, should a user be pressing on the activation buttons. Thus the device is locked and ready to be discarded.

Manual Stop Function

Figure 28:
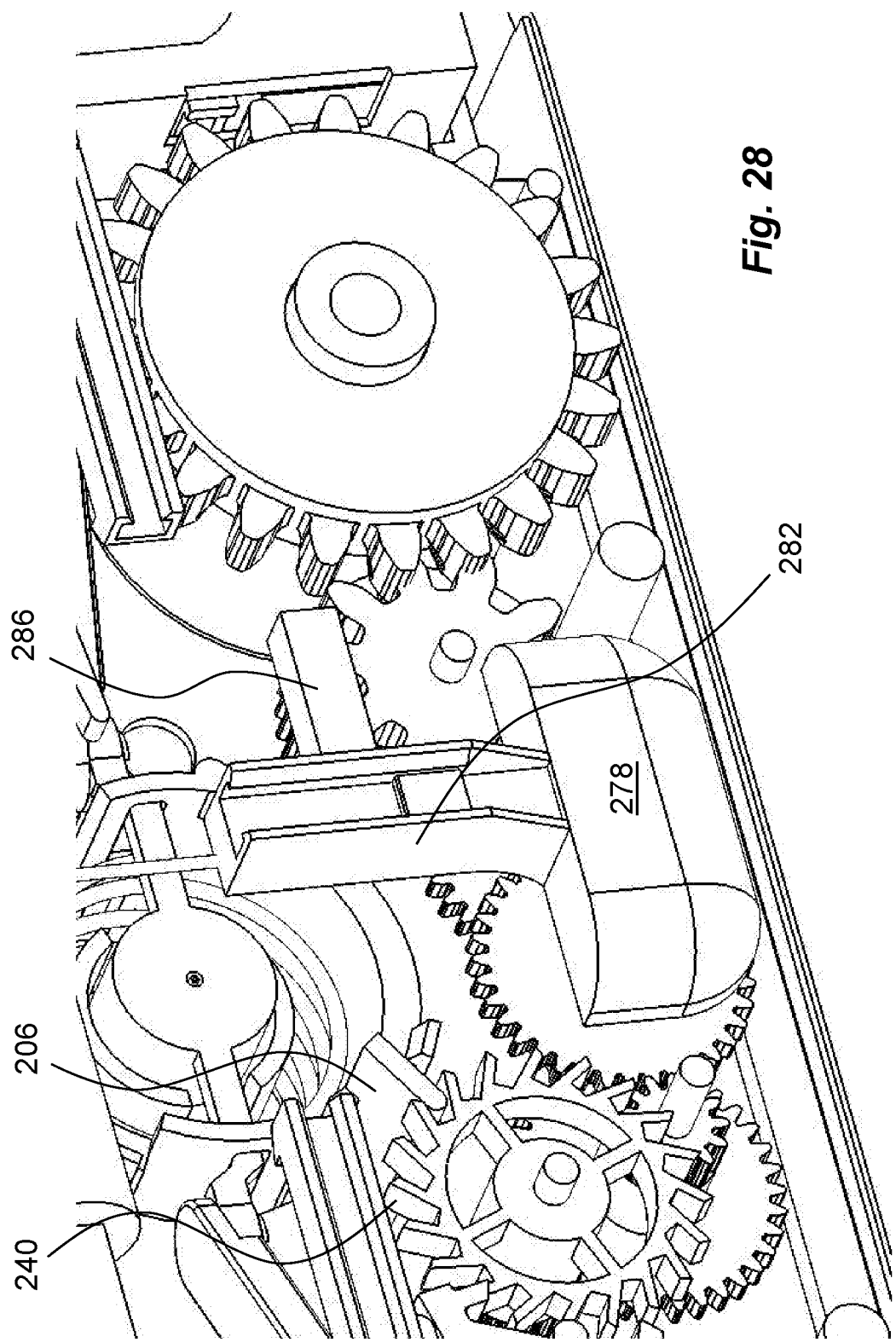

Instead of the automatic stopping of the device, it may be stopped manually by a user. This is done by pressing the actuator element 278 upwards on the distal side of the device. This causes the arm 282 to slide vertically upwards, whereby the beam 286 is also moved upwards. This upwards movement of the beam will cause the needle cover 188 to rotate due to the contact between the beam 286 and the ledge 207, which rotation performs exactly the same functional sequence as with the automatic stop function, FIG. 28. Thus the needle cover 188 will be extended and locked in the extended position and the injection speed control mechanism 212 will be locked by the interaction of the ledge 206 with the escapement wheel 240. The device may now be removed and discarded.

It is to be understood that the embodiment described above and shown in the drawings is to be regarded only as a non-limiting example of the invention and that it may be modified in many ways within the scope of the patent claims.

The invention claimed is:

1. A medicament delivery device, comprising:
   a housing comprising a proximal portion;
   a compartment in the housing for positioning a medicament container;
   an injection needle having a proximal end and movably arranged within the housing and connectable to the medicament container for supplying a dose of medicament;
   a button for activating the medicament delivery device;
   a plunger rod positioned within the housing that operatively engages the medicament container during delivery of the dose of medicament, where the plunger rod moves in a direction transverse to the movement of the proximal end of the injection needle;
   a spring operatively connected to the button mechanism to move the plunger rod to cause delivery of the dose of medicament; and
   a movable needle cover having a central passage, where the proximal end of the injection needle moves relative to and through the central passage when the medicament delivery device is activated,
   wherein delivery of the dose of medicament occurs through the injection needle when the injection needle is penetrating the patient,
   wherein both the needle cover and the central passage move in a proximal direction relative to the proximal portion of the housing to cover the proximal end of the injection needle when the injection needle is removed from a medicament delivery site.

2. The medicament delivery device of claim 1, where the movement of the central passage in the proximal direction is caused by a spring operatively connected to the needle cover.

3. The medicament delivery device of claim 1, where a proximal end of the needle cover is arranged adjacent the housing before and during delivery of the dose of medicament.

4. The medicament delivery device of claim 3, where the proximal end of the needle cover moves to an extended position away from the housing when the injection needle during the delivery of the dose of medicament.

5. The medicament delivery device of claim 1, where the needle cover shields the proximal end of the injection needle to prevent unintentional needle sticks when the injection needle is moved away from a medicament delivery site.

6. The medicament delivery device of claim 1, further comprising a transmission operatively connected to the spring.

7. The medicament delivery device of claim 6, where the transmission comprises gears.

8. The medicament delivery device of claim 1, further comprising a movable hollow spike operably connected to the button wherein, upon activation, the hollow spike moves relative to the medicament container to establish a fluid communication between medicament inside the medicament container and the injection needle.

9. The medicament delivery device of claim 1, wherein the plunger rod comprises a number of segments that are operatively connected to each other.

* * * * *